(12) United States Patent
Hettie et al.

(10) Patent No.: US 10,675,364 B2
(45) Date of Patent: Jun. 9, 2020

(54) RHODOL FLUOROPHORES FOR NEAR-INFRARED IMAGING

(71) Applicants: The Board of Trustees of the Leland Stanford Junior University, Palo Alto, CA (US); THE CURATORS OF THE UNIVERSITY OF MISSOURI, Columbia, MO (US)

(72) Inventors: Kenneth Hettie, Stanford, CA (US); Jessica Klockow, Stanford, CA (US); Timothy Glass, Columbia, MO (US); Frederick T. Chin, Standford, CA (US)

(73) Assignees: THE BOARD OF TRUSTEES OF THE LELAND STANFORD JUNIOR UNIVERSITY, Palo Alto, CA (US); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 135 days.

(21) Appl. No.: 15/738,327

(22) PCT Filed: Jun. 23, 2016

(86) PCT No.: PCT/US2016/038899
§ 371 (c)(1),
(2) Date: Dec. 20, 2017

(87) PCT Pub. No.: WO2016/210054
PCT Pub. Date: Dec. 29, 2016

(65) Prior Publication Data
US 2018/0177897 A1    Jun. 28, 2018

Related U.S. Application Data

(60) Provisional application No. 62/183,292, filed on Jun. 23, 2015.

(51) Int. Cl.
| | |
|---|---|
| A61B 5/00 | (2006.01) |
| A61B 8/00 | (2006.01) |
| A61B 10/00 | (2006.01) |
| A61K 49/00 | (2006.01) |
| C07D 491/052 | (2006.01) |
| G01N 33/58 | (2006.01) |

(52) U.S. Cl.
CPC ...... *A61K 49/0043* (2013.01); *A61K 49/0058* (2013.01); *C07D 491/052* (2013.01); *G01N 33/582* (2013.01); *G01N 2458/00* (2013.01)

(58) Field of Classification Search
CPC ............ A61K 49/0043; A61K 49/0058; C07D 491/052; G01N 33/582; G01N 2458/00
USPC ........................................................ 424/9.6
See application file for complete search history.

(56) References Cited

U.S. PATENT DOCUMENTS

| | | |
|---|---|---|
| 8,569,360 B2 | 10/2013 | Bottaro et al. |
| 8,772,487 B2 | 7/2014 | Chen et al. |
| 8,951,938 B2 | 2/2015 | Chang et al. |
| 2006/0099148 A1* | 5/2006 | Fisher ................ A61K 49/1806 424/9.34 |
| 2009/0111100 A1 | 4/2009 | Lukhtanov et al. |
| 2009/0253143 A1 | 10/2009 | Yang et al. |
| 2014/0051863 A1 | 2/2014 | Chang et al. |

FOREIGN PATENT DOCUMENTS

| | | | | |
|---|---|---|---|---|
| CN | 104710815 A | * | 6/2015 | |
| WO | WO-9516026 A1 | * | 6/1995 | ............. C07K 16/44 |
| WO | WO-2013033396 A2 | * | 3/2013 | ............. A61K 31/69 |
| WO | 2013113279 A1 | | 8/2013 | |

OTHER PUBLICATIONS

Razgulin et al. Chem. Soc. Rev. 2011, 40, 4186-4216.*
Priestman et al. Angew. Chem. Int. Ed. 2012, 51, 7684-7687.*
Labruere et al. Angew. Chem. Int. Ed. 2012, 51, 9344-9347.*
Wu et al. J. Org. Chem. 2008, 73, 8711-8718.*
Cardoso et al. Eur. J. Org. Chem. 2012, 5810-5817.*
International Search Report for PCT/US2016/038899 dated Sep. 6, 2016.

(Continued)

*Primary Examiner* — Michael G. Hartley
*Assistant Examiner* — Sean R Donohue
(74) *Attorney, Agent, or Firm* — Thomas | Horstemeyer, LLP

(57) ABSTRACT

The present disclosure encompasses embodiments of a novel near-infrared-emitting molecular fluorophore and probes incorporating said fluorophore advantageous for in vitro and in vivo research studies. The fluorophore is robust, photostable, and possesses functionalities for easy bioorthogonal conjugation (e.g., click chemistry, hydrazone formation, Diels Alder, Staudinger ligation, etc.). It is biocompatible and emits at 711 nm in aqueous conditions. These fluorophores may be used to fluorescently tag biological molecules or structures of interest, or used as optical reporters (i.e., activatable molecular probes, fluorescent dyes) for specific biomarkers/analytes as they can be switched from "off" to "on." This fluorophore is useful for cellular assays and preclinical small animal imaging as the near-infrared emission is highly penetrating, and the photophysical properties are outstanding. As such, the properties of this class of fluorophores could easily be translated for use in clinical applications.

1 Claim, 18 Drawing Sheets

(56) References Cited

OTHER PUBLICATIONS

Alford, Raphael, et al. "Toxicity of organic fluorophores used in molecular imaging: literature review." Molecular imaging 8.6 (2009): 7290-2009.
Pinto da Silva, Luis, and Joaquim CG Esteves da Silva. "Firefly chemiluminescence and bioluminescence: efficient generation of excited states." ChemPhysChem 13.9 (2012): 2257-2262.
Madan, Damian, et al. "Non-invasive imaging of tumors by monitoring autotaxin activity using an enzyme-activated near-infrated fluorogenic substrate." PloS one 8.11 (2013): e79065.
Schuster, G. B.; Turro, N. J.; Steinmetzer, H. C.; Schaap, A. P.; Faler, G.; Adam, W.; Liu, J. C. Journal of the American Chemical Society 1975, 97, 7110.
Thomas, G. Nature reviews. Molecular cell biology 2002, 3, 753.
Bourne, G. L.; Grainger, D. J. Journal of immunological methods 2011, 364, 101.
Edgington, L E.; Verdoes, M.; Bogyo, M. Current opinion in chemical biology 2011, 15, 798.
Jeon, et al. (2012) "An Efficient Method for Site-specific 18F-Labeling of Biomolecules Using the Rapid Condensation Reaction between 2-Cyanobenzothiazole and Cysteine." Bioconjug. Chem. 23(9):1902-1908.
Dragulsecu-Andrasi, et al. (2013) "Activatable Oligomerizable Imaging Agents for Photoacoustic Imaging of Furin-Like Activity in Living Subjects." J. Am. Chem. Soc. 135:11015-11022.
Huang, et al. (2012) "Radioactive Smart Probe for Potential Corrected Matrix Metalloproteinase Imaging." Bioconjugate Chem. 23:2159-2167.

\* cited by examiner

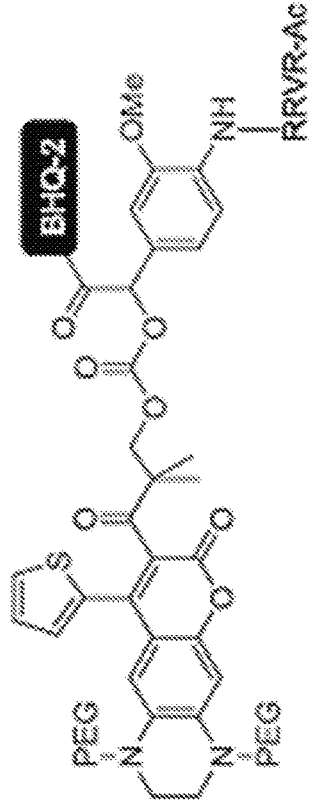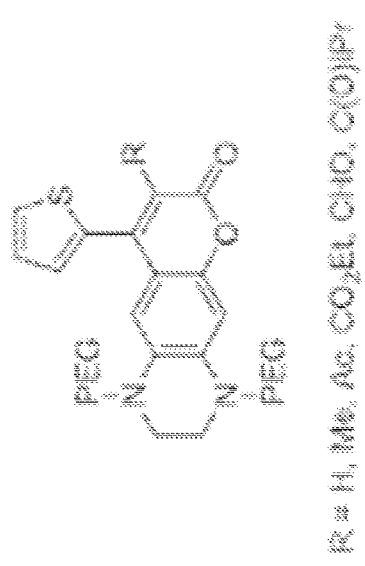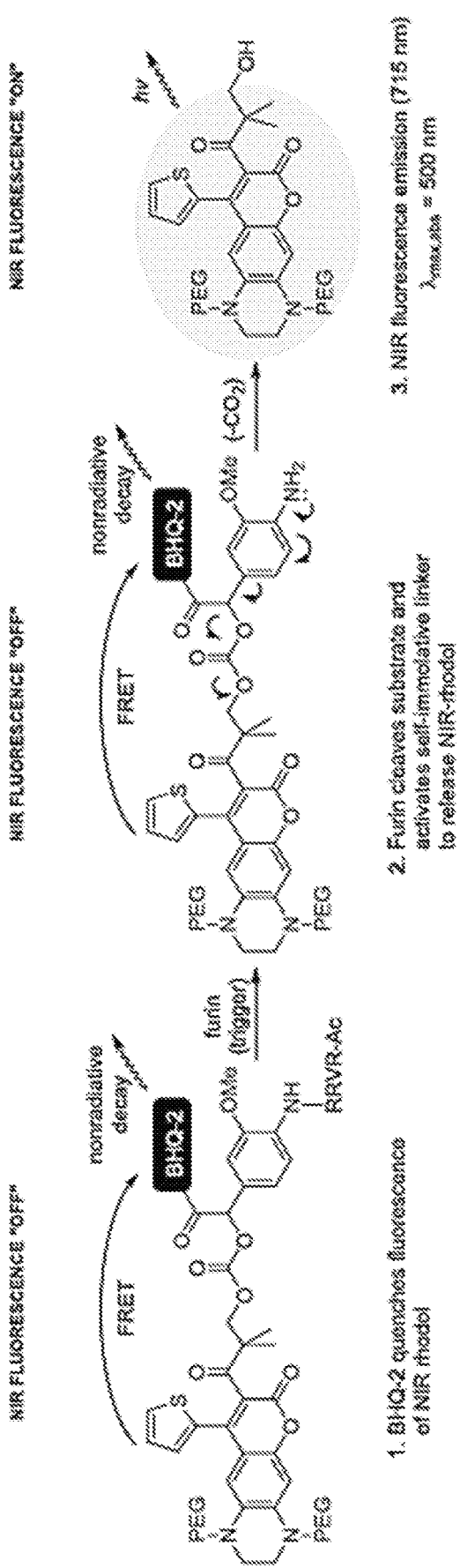
Fig. 10A
Fig. 10B

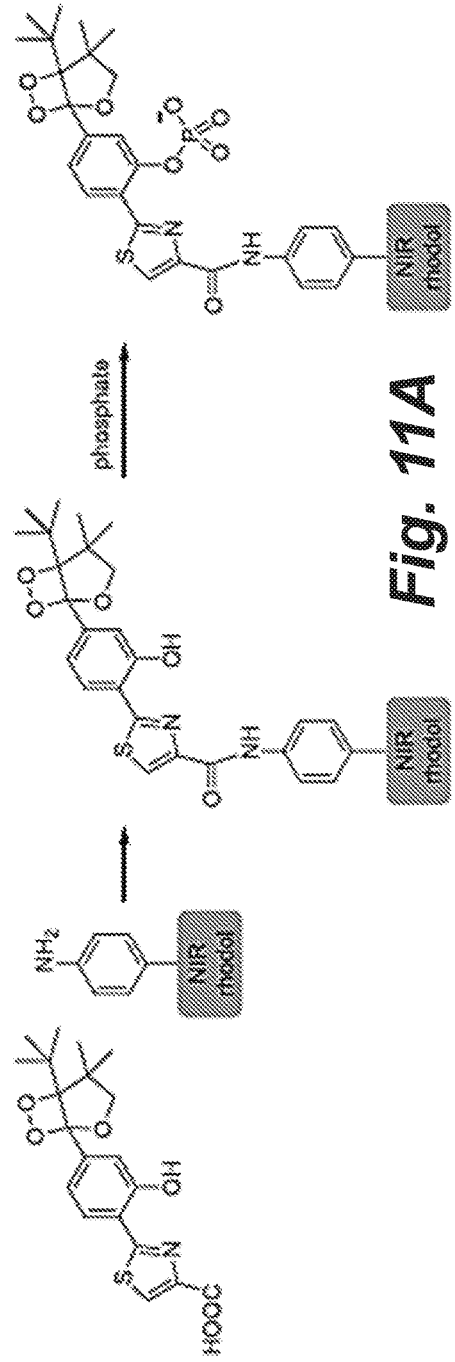
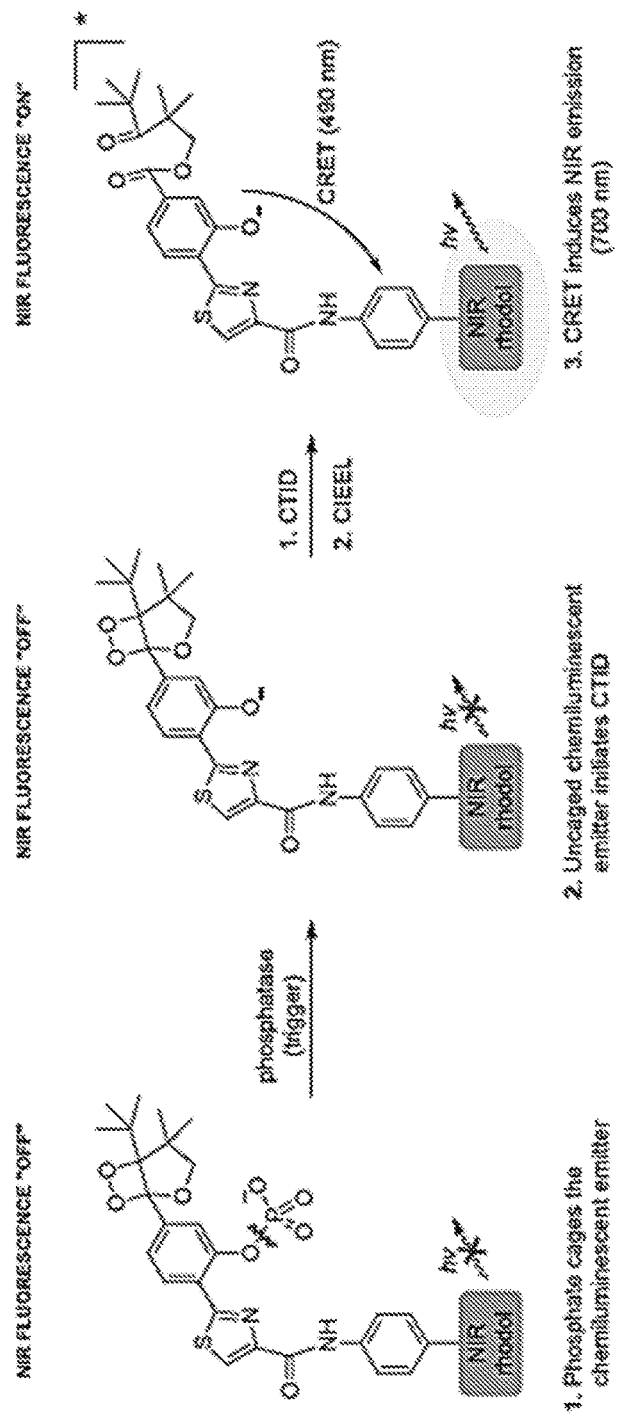
Fig. 11A
Fig. 11B

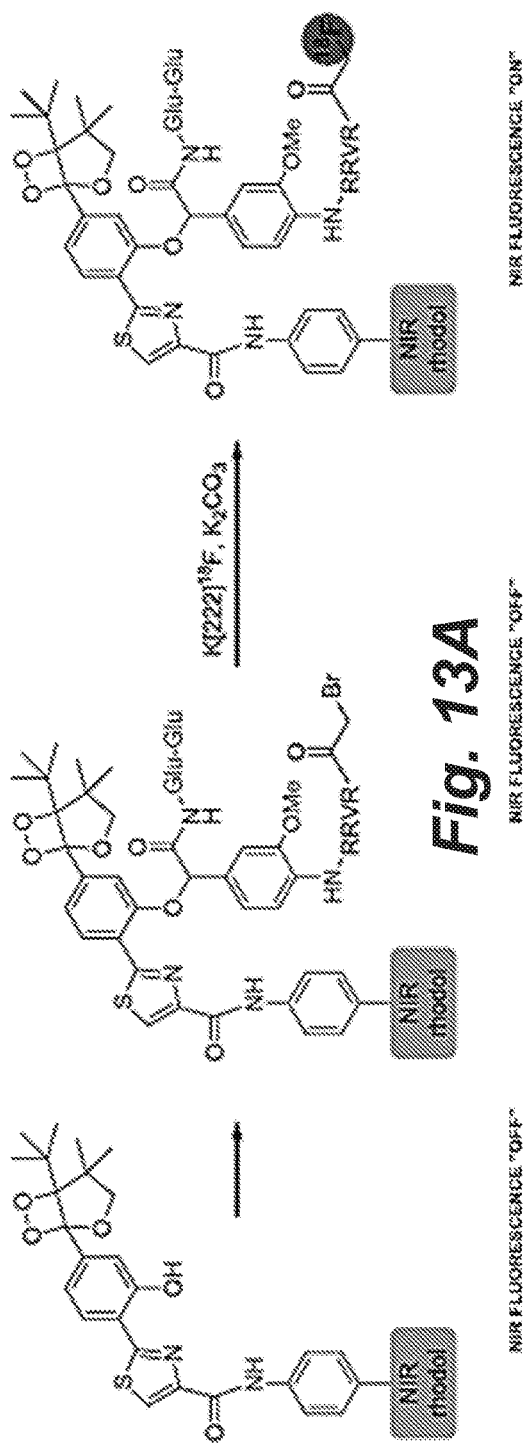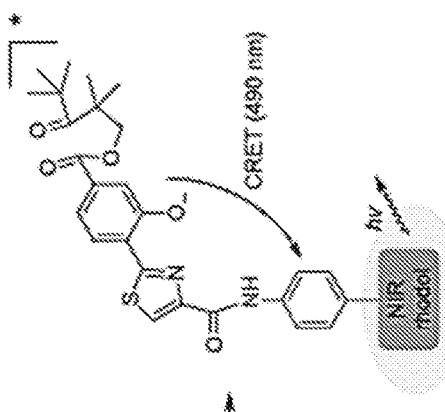
Fig. 13A
Fig. 13B

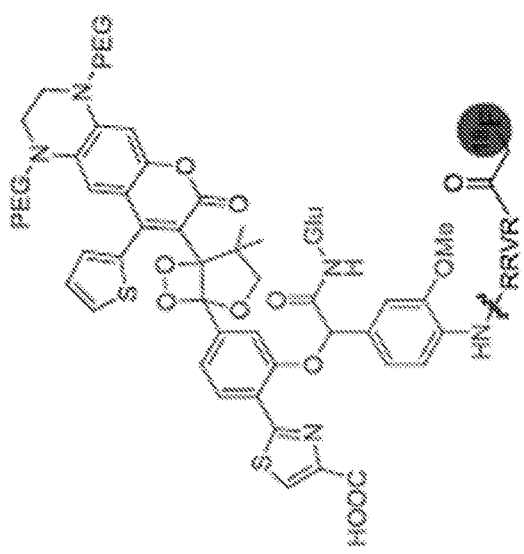
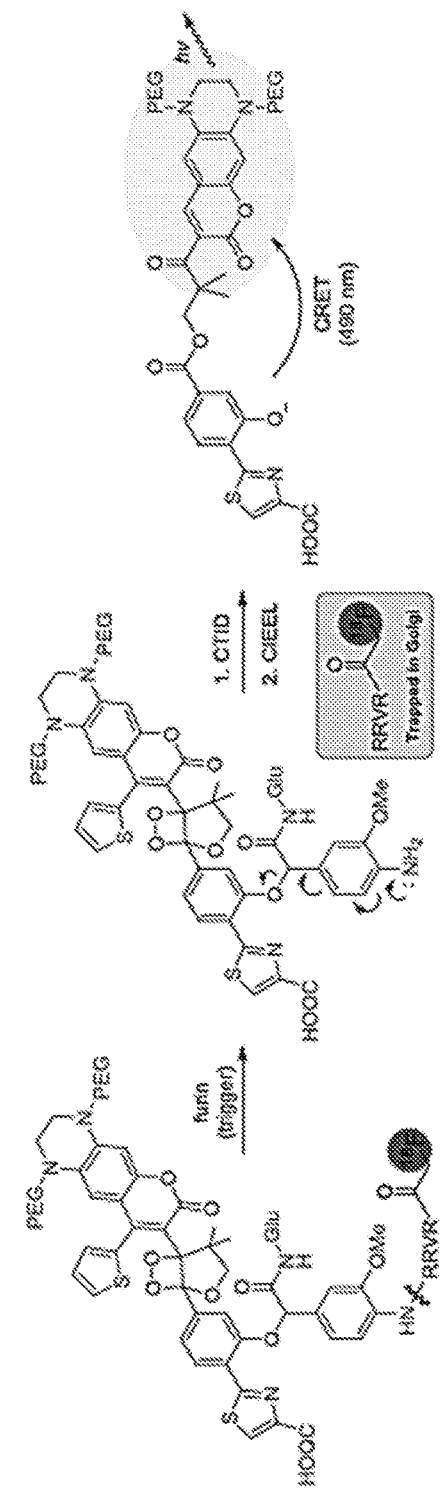
Fig. 15A
Fig. 15B

US 10,675,364 B2

RHODOL FLUOROPHORES FOR NEAR-INFRARED IMAGING

CROSS-REFERENCE TO RELATED APPLICATION

This application is the 35 U.S.C. § 371 national stage application of PCT Application No. PCT/US2016/038899, filed Jun. 23, 2016, where the PCT claims priority to U.S. Provisional Application No. 62/183,292, entitled "NOVEL RHODOL FLUOROPHORES FOR NEAR-INFRARED IMAGING" filed on Jun. 23, 2015, the entireties of which are herein incorporated by reference.

STATEMENT REGARDING FEDERALLY SPONSORED RESEARCH OR DEVELOPMENT

This invention was made with Government support under contract DE-SC0008397 awarded by the Department of Energy, under contract CHE-1112194 awarded by the National Science Foundation and under contract MH096650 awarded by the National Institutes of Health. The Government has certain rights in the invention.

FIELD OF THE DISCLOSURE

The present disclosure relates to delivery of radiolabeled and other ligands to a cell or tissue. The disclosure further relates to methods of ligand delivery to, and imaging of, cells and tissues expressing a gastrin-releasing peptide receptor, in particular prostate cancer cells.

BACKGROUND

Chemiluminescence is a phenomenon where light is emitted from a chemical reaction that produces an excited-state product (Pinto da Silva, et al., (2012) Chemphyschem. 13: 2257). There is significant interest in developing chemiluminescent probes for use in point-of-care diagnostic devices, and for the imaging of biological activities in vitro and in vivo. Chemiluminescent probes can provide detection with high sensitivity and high contrast imaging due to exhibiting no initial background signal as a result of not requiring an external excitation source (Schuster et al., (1975) J. Am. Chem. Soc. 97: 7110). Moreover, chemiluminescent probes confer the additional advantages of not requiring an exogenous enhancer for activation or prior genetic modification for use.

Luminescent probes for use in detection of biological activities have been primarily based on four structures, an acridan ester, peroxalate, luminol, and luciferin platforms. Luminescent probes based on these platforms require in situ formation of an intermediate structure possessing a labile high-energy moiety (e.g., a dioxetanone) that induces the emission of light from the aromatic scaffold upon charge-transfer-induced decomposition (CTID) and subsequent relaxation to the ground state via a chemically-initiated electron exchange (CIEEL) mechanism.

The use of chemiluminescence in analyses has been primarily limited to luminol-based biochemical assays (e.g., Western blots) because the small quantity of light that is generated can be amplified through the use of chemical oxidants ([Ox]) and biological catalysts (enzymes), whereas all chemiluminescent probes based on other platforms are capable of generating only trace amounts of light in aqueous environments (with extremely short lifetimes) that are ill-suited for biological studies. Unfortunately, the enhancers (e.g., horseradish peroxidase) involved with catalyzing luminol-based reactions are typically exogenous to the cellular environment under study and must be administered at extremely high levels of concentration. On the other hand, bioluminescent probes (e.g., D-luciferin) do not require exogenous bioreagents for activation and emission of detectable amounts of light. However, bioluminescent probes do require an expressed enzyme (e.g., luciferase) from transfected genetic material in order to form a high-energy intermediate that is capable of emitting light upon activation, CTID, and CIEEL. As a result, bioluminescent probes are limited to xenograft models for in vivo studies.

A subclass of 1,2-dioxetanes that possess a protected meta-phenolate can be activated by a chemical event which releases a phenolate and triggers the production of light through CIEEL. The chemical event triggers the thermolysis of the 1,2-dioxetane moiety to generate a digroup intermediate that thereby, affords a high-energy species that emits light upon relaxation (electron exchange) to a stable ground state product. Sterically-hindered dioxetanes have been shown to possess greater thermal stability, hence the adamantane substituent (Schuster et al., (1975) J. Am. Chem. Soc. 97: 7110).

Furin is a serine endoprotease that is responsible for proteolytic processing in the body (Thomas, G. (2002) Nature Revs. Mol Cell Biol. 3: 753). Furin is a ubiquitous enzyme that is upregulated in response to various environmental conditions, such as hypoxia and cytokine stimulation, which are characteristics of human tumors (Bourne & Grainger (2011) J. Immunol. Methods 364: 101). It has been shown to be upregulated in several cancers including glioblastomas and is directly correlated with increased cancer aggressiveness due to its role in degradation of the extracellular matrix (ECM) that promotes intravasation and metastasis of tumor cells (Thomas, G. (2002) Nature Revs. Mol Cell Biol. 3: 753). Specifically, furin cleaves C-terminal to basic residues and is specific for the peptide sequence R-X-R/K-R (Arg-X-Arg/Lys-Arg), where "X" is variable (most commonly valine). This sequence can be integrated into a probe that contains an optical reporter in order to monitor both the location and degree of enzyme activity within a specimen. Such "smart" probes have been used in biological systems for monitoring enzymatic activity with great success (Dragulescu-Andrasi et al., (2013) J. Am. Chem. Soc. 135: 11015; Madan et al., 2013) PloS one 8: e79065; Huang et al., (2102) Bioconjugate Chem. 23: 2159; Edgington et al., (2011) Curr. Opinion Chem. Biol. 15: 798).

Despite extensive development of chemiluminescent probes, there remains a long-felt need for fluorophore-based probes that offer advantages over existing probes. For example, greater levels of chemiluminescent light intensity that can be detected in animal tissues at depth within a body is an existing deficiency in the repertoire of available probes.

SUMMARY

The present disclosure encompasses embodiments of a novel near-infrared-emitting molecular fluorophore and probes incorporating said fluorophore advantageous for in vitro and in vivo research studies. The fluorophore is robust, photostable, and possesses functionalities for easy bioorthogonal conjugation (e.g., click chemistry, hydrazone formation, Diels Alder, Staudinger ligation, etc.). It is biocompatible and emits at 711 nm in aqueous conditions. These fluorophores may be used to fluorescently tag biological molecules or structures of interest, or used as optical reporters (i.e., activatable molecular probes, fluorescent dyes) for specific biomarkers/analytes as they can be switched from "off" to "on." This fluorophore is useful for cellular assays and preclinical small animal imaging as the near-infrared emission is highly penetrating, and the photophysical properties are outstanding. As such, the properties of this class of fluorophores could easily be translated for use in clinical applications.

Accordingly, one aspect of the disclosure encompasses embodiments of a compound having the formula (I):

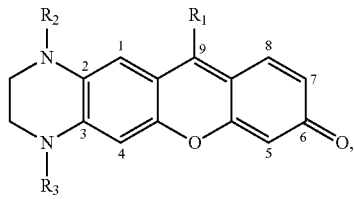

wherein: $R_2$ and $R_3$ can be independently H, an alkyl, an alkenyl, an alkynyl, an alkoxy, an aryl, an aryloxy, a heteroaryl, a cyano, an azido, a nitro, an amino, an amido, a carbonyl, a sulfonyl, a phosphoryl, a halogen, a heteroatom, a polyethylene glycol (PEG), or a self-immolative linker, and wherein the self-immolative linker can be conjugated to any of a fluorescence quencher, a chemiluminescent emitter, an MRI contrast agent or a cell-penetrating peptide, and $R_1$ can be H, an alkyl, an alkenyl, an alkynyl, an alkoxy, an aryl, a substituted aryl, an aryloxy, a heteroaryl, a cyano, an azido, a nitro, an amino, an amido, a carbonyl, a sulfonyl, a phosphoryl, a halogen, a heteroatom, a fluorescence quencher, or a chemiluminescent emitter.

In some embodiments of this aspect of the disclosure, the self-immolative linker can be conjugated to a caging moiety.

In some embodiments of this aspect of the disclosure, the caging moiety is a cleavable enzyme substrate, wherein the cleavable substrate is attached to the self-immolative linker in a position that prevents the emission of a detectable signal from the compound.

In some embodiments of this aspect of the disclosure, the cleavable enzyme substrate ca be a peptide conjugated to the self-immolative linker by a protease.

In some embodiments of this aspect of the disclosure, the protease can be furin.

In some embodiments of this aspect of the disclosure, the cleavable substrate is a phosphate group, an amino group, an alkyl group, a hydroxyl group, a carboxyl group, an amino acid, or a peptide.

In some embodiments of this aspect of the disclosure, the self-immolative linker can be conjugated to a metal chelator and the further comprises a detectable metal ion.

In some embodiments of this aspect of the disclosure, the detectable metal ion can be gadolinium.

In some embodiments of this aspect of the disclosure, the peptide can have the amino acid sequence Arginine-Arginine-Valine-Arginine (RRVR) and be cleavable from the compound by furin.

In some embodiments of this aspect of the disclosure, $R_1$ can be an aryl or a substituted aryl having the formula (II):

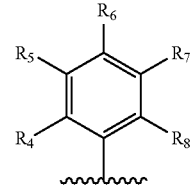

wherein $R_4$-$R_8$ can be independently H, an alkyl, an alkenyl, an alkynyl, an alkoxy, an aryl, an aryloxy, a heteroaryl, a cyano, an azido, a nitro, an amino, an amido, a carbonyl, a sulfonyl, a phosphoryl, a halogen, a heteroatom, a self-immolative linker, or a self-immolative linker conjugated to a fluorescence quencher, a chemiluminescent emitter, or an MRI contrast agent. In some of these embodiments of the aspect of the disclosure, $R_4$-$R_5$ and $R_7$-$R_8$ can be each H and $R_6$ is an alkynyl group, an alkoxy group, an azido group, or an amino group.

In some embodiments of this aspect of the disclosure, the compound can have the formula (III) or (IV)

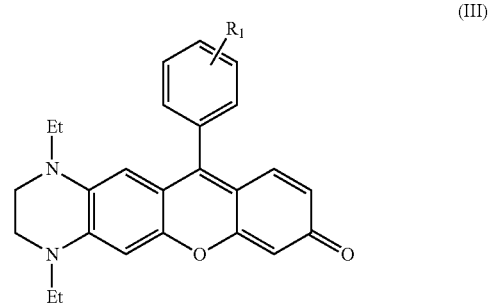

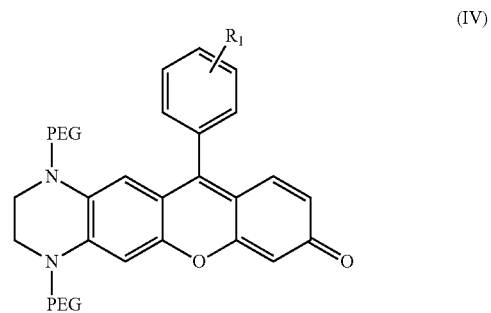

wherein $R_1$ can be an amine, a substituted amine, an azide group, an alkyne, or an acetyl group.

In some embodiments of this aspect of the disclosure, $R_1$ can be selected from —$NH_2$, —$N_3$, —$(CH_2)_nC{\equiv}C$, or —COOMe. In some embodiments of this aspect of the disclosure, said probe can be selected from the formula A, B, C, D:

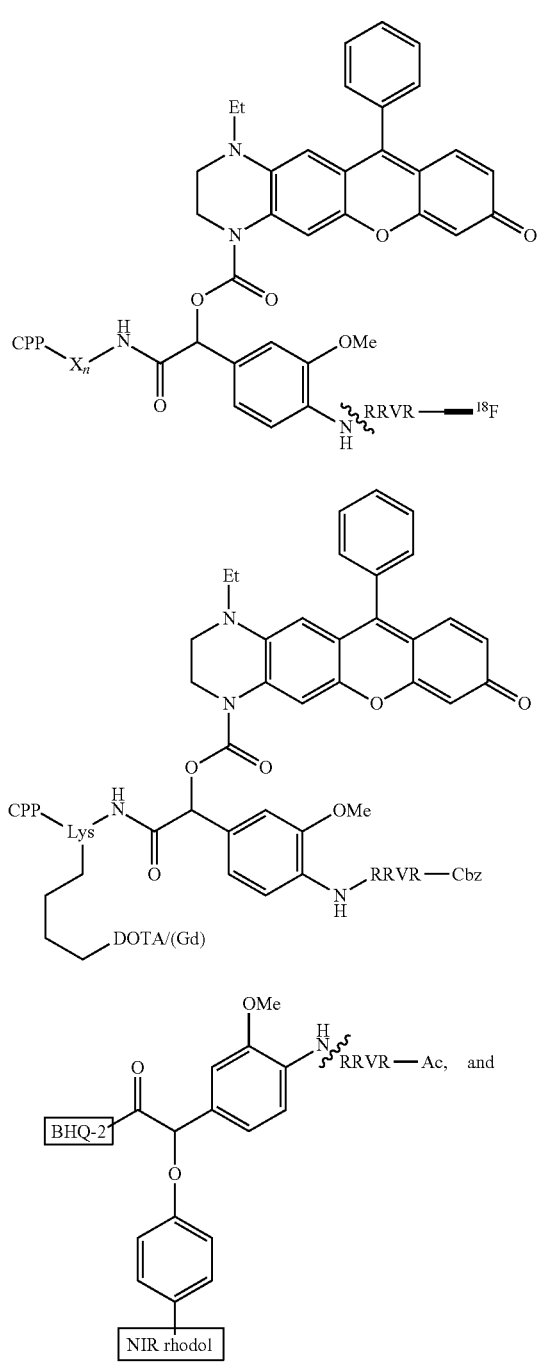

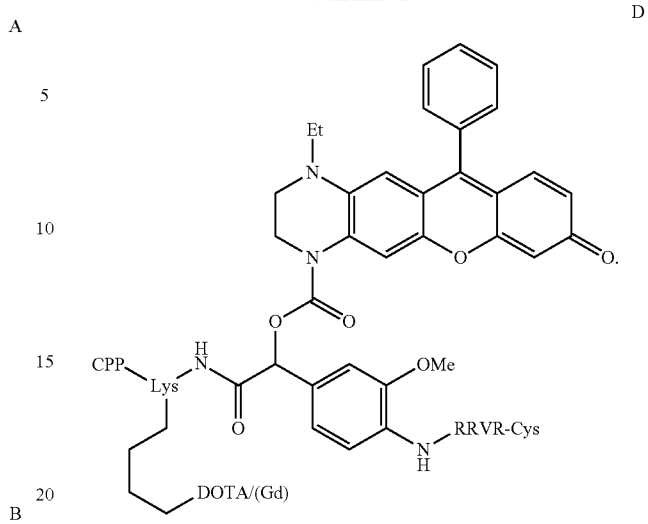

BRIEF DESCRIPTION OF THE DRAWINGS

Many aspects of the disclosure can be better understood with reference to the following drawings.

FIG. 10A illustrates an embodiment of a furin-activated NIR-emitting coumarin probe.

FIG. 10B illustrates the mechanism of fluorescence emission from a furin-activated NIR-emitting coumarin probe.

FIG. 11A illustrates an embodiment of an enzyme-activated NIR-emitting CRET probe incorporating an NIR rhodol of the disclosure.

FIG. 11B illustrates an example of the rhodol fluorophore as a chemiluminescence resonance energy transfer (CRET) acceptor. The fluorescence emission of the rhodol is "off" until enzyme activation (or other trigger) activates the chemiluminescent emitter. Energy then transfers from the chemiluminescent emitter to the rhodol fluorophore which emits in the NIR wavelength range. CTID=charge-transfer-induced decomposition. CIEEL=chemically initiated electron-exchange luminescence.

FIG. 13A illustrates an embodiment of a multimodal furin-activated NIR-emitting CRET/$^{18}$F probe incorporating an NIR rhodol of the disclosure.

FIG. 13B illustrates the mechanism of NIR emission from a multimodal furin-activated NIR-emitting CRET/$^{18}$F probe incorporating an NIR rhodol of the disclosure. The probe consists of: a rhodol fluorophore, a self-immolative linker, an enzyme substrate, a chemiluminescent emitter, and a radioactive label. First, the non-fluorescent probe will be radiolabeled. Then, the probe will be injected into the specimen. It will penetrate the blood-brain barrier (BBB) due to the cell penetrating peptide (CPP)/targeting ligand and enter the GBM cell to be cleaved by furin. Enzymatic cleavage activates the self-immolative linker which releases the CL emitter. Energy transfers from the CL emitter to the rhodol fluorophore to produce NIR fluorescence. The cleaved radiolabel is positively charged (due to the arginines) and will stay trapped inside the cell (most likely in the Golgi), which results in a high PET signal contrast. RRVR=Arg-Arg-Val-Arg.

FIG. 15A illustrates an embodiment of a multi-modal imaging with a NIR-emitting coumarin probe directly integrated into a chemiluminescent system.

FIG. 15B illustrates the mechanism of NIR emission from a multi-modal imaging with a NIR-emitting coumarin probe directly integrated into a chemiluminescent system via release of an $^{18}$F-bearing self-immolative linker.

DETAILED DESCRIPTION

Figure 1A:
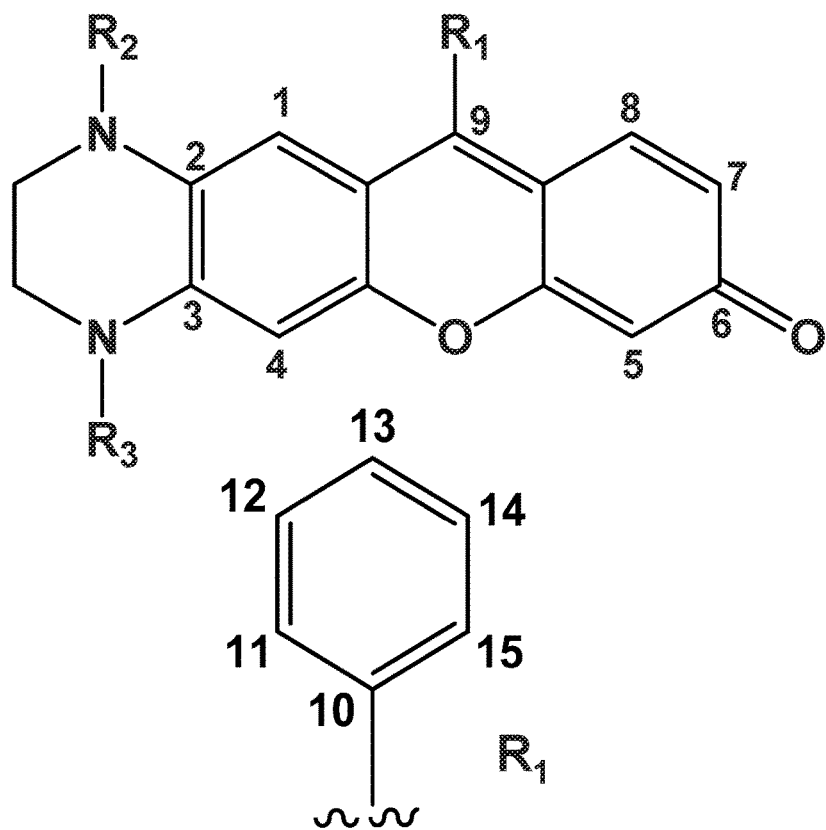
FIG. 1A illustrates the structure and numbering of the THQ-based rhodol fluorophore of the disclosure. Key sites on both the scaffold (top) and the pendant substituent (bottom) allow for modulating the fluorescence response or adding various handles that can undergo bioconjugate or biorthogonal chemistries.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Numerical ranges recited herein by endpoints include all numbers and fractions subsumed within that range (e.g. 1 to 5 includes 1, 1, 5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made.

Prior to describing the various embodiments, the following definitions are provided and should be used unless otherwise indicated.

Abbreviations

CTID, charge-transfer-induced decomposition; CIEEL, chemically-initiated electron exchange; PEG, polyethylene glycol; RRVR, cell-penetrating peptide Arginine-Arginine-Valine-Arginine; THQ, 1,2,3,4-tetrahydroquinoxaline; NIR, Near-Infra-Red; CPP, cell penetrating peptide; BBB, blood-brain barrier; GBM, glioblastoma; CRET, chemiluminescence resonance energy transfer;

FRET, fluorescence resonance energy transfer; PET, positron emission tomography; CT, computerized tomography, MRI, magnetic resonance imaging; ICT, intramolecular charge transfer.

Definitions

In describing and claiming the disclosed subject matter, the following terminology will be used in accordance with the definitions set forth below.

The term "acetylamino" shall mean any primary or secondary amino that is acetylated. Examples of such include, but are not limited to, acetamide and the like.

The term "acid anhydride" as used herein refers to an anhydride of an organic acid and includes, but is not limited to acetic anhydride (($CH_3C=O)_2O$ or $Ac_2O$) and benzoic anhydride (($C_6H_5C=O)_2O$).

The term "activatable probe" as used herein refers to a probe monomer of the disclosure that includes a blocking, or capping, peptide that can be cleaved from the probe. Upon cleavage, the probe may then cyclize and aggregate to generate a non-aggregation probe structure. The term "activatable probe" may further refer to a probe of the disclosure that includes a detectable imaging moiety that is a fluorescence emitter and a detachable quencher moiety that may be, for example, attached to the capping moiety. Upon cleavage of the capping moiety from the probe, and hence activation of said probe, the quencher is displaced from the vicinity of the fluorophore imaging moiety and a detectable signal may be generated.

The term "acyl" as used herein refers to an organic acid group wherein the —OH of the carboxyl group has been replaced with another substituent (i.e., as represented by RCO—, wherein R is an alkyl or an aryl group as defined herein). The term "acyl" specifically includes arylacyl groups, such as an acetylfuran and a phenacyl group. Specific examples of acyl groups include a carbonyl or thiocarbonyl group bonded to a group selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, berizoyloxy, p-methoxybenzoyloxy, and substituted acyloxy such as alkoxyalkyl and haloalkoxy), aryl, halo, heterocyclyl, heteroaryl, sulfonyl (e.g. allylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" groups are formyl, acetyl, 2-chloroacetyl, 2-bromacetyl, benzoyl, trifluoroacetyl, phthaloyl, malonyl, nicotinyl, and the like. The term "acyl" as used herein refers to a group —$C(O)R_{26}$, where $R_{26}$ is hydrogen, alkyl, cycloalkyl, cycloheteroalkyl, aryl, arylalkyl, heteroalkyl, heteroaryl, and heteroarylalkyl.

The term "acylamino" as used herein refers to an acyl-NH— group wherein acyl is as previously described.

The term "acyloxyl" as used herein refers to an acyl-O— group wherein acyl is as previously described.

The term "alkenyloxy" as used herein refers to linear or branched oxy-containing groups having an alkenyl portion of about 2 to 10 carbon atoms, such as an ethenyloxy or propenyloxy group. An alkenyloxy group may be a "lower alkenyloxy" group having about 2 to 6 carbon atoms. Examples of alkenyloxy groups include without limitation ethenyloxy, propenyloxy, butenyloxy, and isopropenyloxy alkyls. An "alkenyloxy" group may be substituted with one or more substitutents disclosed herein including halo atoms, such as fluoro, chloro or bromo, to provide "haloalkenyloxy" groups (e.g. trifluoroethenyloxy, fluoroethenyloxy, difluoroethenyloxy, and fluoropropenyloxy).

The term "alkoxy" refers to a linear or branched oxy-containing group having an alkyl portion of one to about ten carbon atoms, such as a methoxy group, which may be substituted. In aspects of the disclosure an alkoxy group may comprise about 1-10, 1-8, 1-6 or 1-3 carbon atoms. In embodiments of the disclosure, an alkoxy group comprises about 1-6 carbon atoms and includes a $C_1$-$C_6$ alkyl-O-group wherein $C_1$-$C_6$ alkyl has the meaning set out herein. Alkoxy groups include without limitation methoxy, ethoxy, propoxy, butoxy, isopropoxy and tert-butoxy alkyls. An "alkoxy" group may, optionally be substituted with one or more substitutents disclosed herein including alkyl atoms to provide "alkylalkoxy" groups; halo atoms, such as fluoro, chloro or bromo, to provide "haloalkoxy" groups (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxy-alkyl" groups (e.g. fluoromethoxymethyl, chloromethoxy-ethyl, trifluorornethoxymethyl, difluoromethoxyethyl, and trifluorocthoxymethyl).

The term "alkoxycarbonyl" as used herein refers to an alkyl-O—CO— group. Exemplary alkoxycarbonyl groups include methoxycarbonyl, ethoxycarbonyl, butyloxycarbonyl, and t-butyloxycarbonyl.

The terms "alkoxyl" or "alkoxyalkyl" as used herein refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkyl", either alone or within other terms such as "thioalkyl" and "arylalkyl", as used herein, means a monovalent, saturated hydrocarbon group which may be a straight chain (i.e. linear) or a branched chain. An alkyl group for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl groups include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl group is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl group may be optionally substituted with substituents as defined herein at positions that do not significantly interfere with the preparation of compounds of the disclosure and do not significantly reduce the efficacy of the compounds. In certain aspects of the disclosure, an alkyl group is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

The term "alkenyl" as used herein refers to an unsaturated, acyclic branched or straight-chain hydrocarbon group comprising at least one double bond. An alkenyl group may contain from about 2 to 24 or 2 to 10 carbon atoms, in particular from about 3 to 8 carbon atoms and more particularly about 3 to 6 or 2 to 6 carbon atoms. Suitable alkenyl groups include without limitation ethenyl, propenyl (e.g., prop-1-en-1-yl, prop-1-en-2-yl, prop-2-en-1-yl (allyl), and prop-2-en-2-yl), buten-1-yl, but-1-en-2-yl, 2-methyl-prop-1-en-1-yl, but-2-en-1-yl, but-2-en-2-yl, buta-1,3-dien-1-yl, beta-1,3-dien-2-3/1, hexen-1-yl, 3-hydroxyhexen-yl, hepten-1-yl, and octen-1-yl, and the like. An alkenyl group may be optionally substituted similar to alkyl.

The term "alkylcarbamoyl" as used herein refers to a R'RN—CO— group wherein one of R and R' is hydrogen and the other of R and R' is alkyl and/or substituted alkyl as previously described.

The term "alkylene" as used herein refers to a linear or branched group having from about 1 to 10, 1 to 8, 1 to 6, or 2 to 6 carbon atoms and having attachment points for two or more covalent bonds. Examples of such groups are methylene, ethylene, propylene, butylene, pentylene, hexylene, ethylidene, methylethylene, and isopropylidene. When an alkenylene group is present as a substituent on another group it is typically considered to be a single substituent rather than a group formed by two substituents.

The term "alkenylene" as used herein refers to a linear or branched group having from about 2 to 10, 2 to 8 or 2 to 6 carbon atoms, at least one double bond, and having attachment points for two or more covalent bonds. Examples of alkenylene groups include 1,1-vinylidene (—$CH_2$=C—), 1,2-vinylidene (—CH=CH—), and 1,4-butadienyl (—CH=CH—CH=CH—).

The term "amino" as used herein, alone or in combination, refers to a group where a nitrogen atom (N) is bonded to three substituents being any combination of hydrogen, hydroxyl, alkyl, cycloalkyl, alkenyl, alkynyl, aryl, silyl, heterocyclic, or heteroaryl which may or may not be substituted. Generally an "amino group" has the general chemical formula —$NR_{20}R_{21}$ where $R_{20}$ and $R_{21}$ can be any combination of hydrogen, hydroxyl, alkyl, cycloalkyl, alkoxy, alkenyl, alkynyl, aryl, carbonyl carboxyl, amino, silyl, heteroaryl, or heterocyclic which may or may not be substituted. Optionally one substituent on the nitrogen atom may be a hydroxyl group (—OH) to provide an amine known as a hydroxylamine. Illustrative examples of amino groups are amino alkylamino, acylamino, cycloamino, acycloalkylamino, arylamino, arylalkylamino, and lower alkylsilylamino, in particular methylamino, ethylamino, dimethylamino, 2-propylamino, butylamino, isobutylamino, cyclopropylamino, benzylamino, allylamino, hydroxylamino, cyclohexylamino, piperidinyl, hydrazinyl, benzylamino, diphenylmethylamino, tritylamino, trimethylsilylamino, and dimethyl-tert.-butylsilyiamino, which may or may not be substituted.

The term "aralkoxycarbonyl" as used herein refers to an aralkyl-O—CO— group. An exemplary aralkoxycarbonyl group is benzyloxycarbonyl.

The term "aralkyl" as used herein refers to an aryl-alkyl-group wherein aryl and alkyl are as previously described, and included substituted aryl and substituted alkyl. Exemplary aralkyl groups include benzyl, phenylethyl, and naphthylmethyl.

The term "aralkyloxyl" as used herein refers to an aralkyl-O— group wherein the aralkyl group is as previously described. An exemplary aralkyloxyl group is benzyloxyl.

The term "aroyl" as used herein refers to aryl groups, as defined above, attached to a carbonyl group as defined herein, including without limitation benzoyl and toluoyl. An aroyl group may be optionally substituted with groups as disclosed herein.

The term "aroylamino" as used herein refers to an aroyl-NH— group wherein aroyl is as previously described.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

An aryl group may be optionally substituted with one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, acylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfenic acid, alkysulfonyl, sulfonamido, aryloxy and the like. A substituent may be further substituted by hydroxy, halo, alkyl, alkoxy, alkenyl, alkynyl, aryl or aralkyl. In aspects of the disclosure an aryl group is substituted with hydroxyl, alkyl, carbonyl, carboxyl, thiol, amino, and/or halo.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aryloxycarbonyl" as used herein refers to an aryl-O—CO— group. Exemplary aryloxycarbonyl groups include phenoxy- and naphthoxy-carbonyl.

The term "aryloxyl" as used herein refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl hexyloxyl, napthyloxy, quinolyloxy, isoquiriolizinyloxy, and the like.

The term "arylalkoxy" as used herein refers to an aryl group attached to an alkoxy group. Representative examples of arylalkoxy groups include, but are not limited to, 2-phenylethoxy, 3-naphth-2-ylpropoxy, and 5-phenylpentyloxy.

The term "caging group" as used herein refers to a moiety that can be employed to reversibly block, inhibit, or interfere with the activity (e.g., the biological activity) of a molecule (e.g., a polypeptide, a nucleic acid, a small molecule, a drug, and the like). Typically, one or more caging groups are associated (covalently or noncovalently) with the molecule but do not necessarily surround the molecule in a physical cage. For example, a single caging group covalently attached to a phosphate side chain of a nucleoside required for the catalytic activity of an enzyme or physiological process can block the activity of the enzyme. The enzyme would thus be caged even though not physically surrounded by the caging group. Caging groups can be, for example, relatively small moieties such as carboxyl nitrobenzyl, 2-nitrobenzyl, nitroindoline, hydroxyphenacyl, DMNPE, quinilones including bromoquinilones and derivatives thereof, or the like, or they can be, e.g., large bulky moieties such as a protein or a bead. Caging groups can be removed from a molecule, or their interference with the molecule's activity can be otherwise reversed or reduced, by exposure to an appropriate type of uncaging energy and/or exposure to an uncaging chemical, enzyme, or the like. The caging groups of the present disclosure may be released from the blocked or "caged" nucleoside triphophoester (uncoupled) by photolysis following two-photon excitation.

The term "carbocylic" as used herein includes groups derived from a saturated or unsaturated, substituted or unsubstituted 5 to 14 member organic nucleus whose ring forming atoms (other than hydrogen) are solely carbon. Examples of carbocyclic groups are cycloalkyl, cycloalkenyl, aryl, in particular phenyl, naphthyl, norbornanyl, bicycloheptadienyl, toluoyl, xylenyl, indenyl, stilbenzyl, terphenylyl, diphenylethylenyl, phenylcyclohexyl, acenapththylenyi, anthracenyl, biphenyl, bibenzylyl, and related bibenzylyl homologs, octahydronaphthyl, tetrahydronaphthyl, octahydroquinolinyl, dimethoxytetrahydronaphthyl and the like.

The term "carbamoyl" as used herein, alone or in combination, refers to amino, monoalkylamino, dialkylamino, monocycloalkylamino, alkyleycloalkylamino, and dicycloalkylaxaino groups, attached to one of two unshared bonds in a carbonyl group.

The term "carbonyl" as used herein refers to a carbon group having two of the four covalent bonds shared with an oxygen atom. The term "carbonyl" as used herein refers to the —(C=O)— group.

The term "carboxamide" as used herein refers to the group —CONH—.

The term "carboxyl" as used herein, alone or in combination, refers to —C(O)OR— or —C(=O)OR wherein R is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. In aspects of the disclosure, the carboxyl groups are in an esterified form and may contain as an esterifying group lower alkyl groups. In particular aspects of the disclosure, —C(O)OR provides an ester or an amino acid derivative. An esterified form is also particularly referred to herein as a "carboxylic ester". In aspects of the disclosure a "carboxyl" may be substituted, in particular substituted with allyl which is optionally substituted with one or more of amino, amine, halo, alkylamino, aryl, carboxyl, or a heterocyclic. Examples of carboxyl groups are methoxycarbonyl, butoxycarbonyl, tert.alkoxycarbonyl such as tert.butoxycarbonyl, arylmethyoxycarbonyl having one or two aryl groups including without limitation phenyl optionally substituted by for example lower alkyl, lower alkoxy, hydroxyl, halo, and/or nitro, such as benzyloxycarbonyl, methoxybenzyloxycarbonyl, diphenylmethoxycarbonyl, 2-bromoethoxycarbonyl, 2-iodoethoxycarbonyltert.butylcarborlyl, 4-nitrobenzyloxycarbonyl, diphenylmethoxy-carbonyl, benzhydroxycarbonyl, di-(4-methoxyphenyl-methoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. The silicon substituent in such compounds may be substituted with lower alkyl (e.g. methyl), alkoxy (e.g. methoxy), and/or halo (e.g. chlorine). Examples of silicon substituents include trimethylsilyi and dimethyltert.butylsilyl. In aspects of the disclosure, the carboxyl group may be an alkoxy carbonyl, in particular methoxy carbonyl, ethoxy carbonyl, isopropoxy carbonyl, t-butoxycarbonyl, t-pentyloxycarbonyl, sir heptyloxy carbonyl, especially methoxy carbonyl or ethoxy carbonyl.

The term "cell-penetrating peptide" as used herein refers to a peptide of about 5 to about 30 amino acids that is able to penetrate cell membranes and to translocate different cargoes into cells.

Examples of useful transport peptides are sequences derived from homeodomains of certain transcription factors, as well as so-called Tat-derived peptides and peptides based on signal sequences. Another group of peptides that have been shown to be able to transport across the cellular membrane, when coupled to a hydrophobic moiety, are modified receptors, in particular G protein coupled receptors. Attachment of a hydrophobic moiety to peptides derived from the third intracellular loop of a seven-transmembrane receptor yields cellular translocation of said chimeric peptides. These pepducines are membrane inserting, membrane-tethered chimeric peptides and require the presence of their cognate receptor for activity and are highly selective for receptor type.

As found for many G-protein coupled receptors, some synthetic peptides, derived from their intracellular loops, influence receptor-G-protein interactions in membrane preparation. Thus, said cell-penetrating functional protein-mimicking peptide can be derived from or designed to resemble a mammalian receptor, such as a receptor belonging to a protein family which can be classified based on its member's structure and their function and comprises channel receptors, tyrosine kinase receptors, guanylate cyclase receptors, serine/threonine kinase receptors, cytokine receptors, and receptors coupled to guanosine triphosphate (GTP)-binding proteins (G protein-coupled receptors: GPCRS).

Nonetheless, a cell-penetrating functional protein-mimicking peptide can equally well be derived from or be designed to resemble any other cellular effector, such as an enzyme, channel, hormone, transcription factor, receptor agonist or antagonist, transporter, or ligand, and can e.g. be derived from or resemble platelet-activating factor (PAF), CGRP, thyroid-stimulating hormone (TSH), luteinizing hormone (LH), or follicle-stimulating hormone (FSH). The term "chelator" as used herein refers to a molecular moiety that may form ionic bonds to an anion and in particular to metallic ions that have at least two positive charges thereon. Chelating agents containing paramagnetic metals for use in magnetic resonance imaging can also be employed as ancillary agents. Typically, a chelating agent containing a paramagnetic metal is associated with a coating on the nanoparticles. The chelating agent can be coupled directly to one or more of components of the coating layer, such as a polyaspartate coat. Suitable chelating agents include a variety of multi-dentate compounds including EDTA, DPTA, DOTA, and the like. These chelating agents can be coupled directly to functional amino groups of a polyaspartate coat of the nanoparticles.

The term "cyano" as used herein refers to a carbon group having three of four covalent bonds shared by a nitrogen atom, in particular —CN. A cyano group may be substituted with substituents described herein.

The terms "cyclic" and "cycloalkyl" as used herein refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur, or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloaliphatic" as used herein refers to a cycloalkane possessing less than 8 carbons or a fused ring system consisting of no more than three fused cycloaliphatic rings. Examples of such groups include, but are not limited to, decalin and the like.

The term "cycloalkenyl" as used herein refers to groups comprising about 4 to 16, 2 to 15, 2 to 10, 2 to 8, 4 to 10, 3 to 8, 3 to 7, 3 to 6, or 4 to 6 carbon atoms, one or more carbon-carbon double bonds, and one, two, three, or four rings wherein such rings may be attached in a pendant manner or may be fused. In certain aspects of the disclosure the cycloalkenyl groups are "lower cycloalkenyl" groups having three to seven carbon atoms. Examples of cycloalkenyl groups include without limitation cyclobutenyl, cyclopentenyl, cyclohexenyl and cycloheptenyl. A cycloalkenyl group may be optionally substituted with groups as disclosed herein, in particular 1, 2, or 3 substituents which may be the same or different.

The term "cycloalkoxy" as used herein refers to cycloalkyl groups (in particular, cycloalkyl groups having 3 to 15, 3 to 8 or 3 to 6 carbon atoms) attached to an oxy group. Examples of cycloalkoxy groups include cyclohexoxy and cyclopentoxy. A cycloalkoxy group may be optionally substituted with groups as disclosed herein.

The term "cycloalkyl" as used herein refers to groups having from about 3 to 15, 3 to 10, 3 to 8, or 3 to 6 carbon atoms and containing one, two, three, or four rings wherein such rings may be attached in a pendant manner or may be fused. In aspects of the disclosure, "cycloalkyl" refers to an optionally substituted, saturated hydrocarbon ring system containing 1 to 2 rings and 3 to 7 carbons per ring which may be further fused with an unsaturated C3-C7 carbocylic ring. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like, or multiple ring structures such as adamantanyl, and the like. Tin certain aspects of the disclosure the cycloalkyl groups are "lower cycloalkyl" groups having from about 3 to 10, 3 to 8, 3 to 6, or 3 to 4 carbon atoms, in particular cyclopropyl, cyclobutyl, cyclopentyl, cyclohexyl and cycloheptyl. The term "cycloalkyl" also embraces groups where cycloalkyl groups are fused with aryl groups or heterocyclyl groups. A cycloalkyl group may be optionally substituted with groups as disclosed herein.

The term "detectable moiety" as used herein refers to a label molecule (isotopic or non-isotopic) which is incorporated indirectly or directly into a liposomal nanoparticle according to the disclosure, wherein the label molecule facilitates the detection of the nanoparticle in which it is incorporated. Thus, "detectable moiety" is used synonymously with "label molecule". Label molecules, known to those skilled in the art as being useful for detection, include chemiluminescent or fluorescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

The term "dialkylamino" as used herein refers to an —NRR' group wherein each of R and R' is independently an alkyl group and/or a substituted alkyl group as previously described. Exemplary alkylamino groups include ethylmethylamino, dimethylamino, and diethylamino.

The term "dialkylcarbamoyl" as used herein refers to a R'RN—CO— group wherein each of R and R' is independently alkyl and/or substituted alkyl as previously described.

The term "diasteriomer" as used herein refers to a compound of the disclosure can contain one or more asymmetric centers and may give rise to enantiomers, diasteriomers, and other stereoisomeric forms which may be defined in terms of absolute stereochemistry as (R)- or (S)-. Thus, compounds of the disclosure include all possible diasteriomers and enantiomers as well as their racemic and optically pure forms. Optically active (R)- and (S)-isomers may be prepared using chiral synthons or chiral reagents, or resolved using conventional techniques. When a compound of the disclosure contains centers of geometric asymmetry, and unless specified otherwise, it is intended that the compounds include both E and A geometric isomers. All tautomeric forms are also included within the scope of a compound of the disclosure.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HiLyte™ Fluors (AnaSpec), and DyLite™ Fluors (Pierce, Inc).

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). FRET techniques are well known in the art, and can be readily used to detect the titanium oxide-bound peptides of the present disclosure. See for example U.S. Pat. Nos. 5,668,648, 5,707,804, 5,728,528, 5,853,992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

The terms "halo," "halide," or "halogen" as used herein refer to fluoro, chloro, bromo, and iodo groups.

The term "heteroaryl" as used herein refers to fully unsaturated heteroatom-containing ring-shaped aromatic groups having at least one heteroatom selected from carbon, nitrogen, sulfur and oxygen. A heteroaryl group may contain one, two or three rings and the rings may be attached in a pendant manner or may be fused. In aspects of the disclosure the term refers to fully unsaturated hetoreatom-containing ring-shaped aromatic groups having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" groups, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, benzimidazolyl, quinolyl, isoquinolyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl; purinyl, benzimidazolyl, quinolinyl, isoquinolinyl, beazotriazolyl, tetrazolopyridazinyl and the like; an unsaturated 3 to 6-membered heteromonocyclic group containing an oxygen atom, in particular, 2-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes groups where heterocyclic groups are fused with aryl groups, in particular bicyclic groups such as benzofuranyl, benzothiophenyl, phthalazinyl, chromenyl, xanthenyl, and the like. A heteroaryl group may be optionally substituted with groups as disclosed herein, for example with an alkyl, amino, halogen, etc., in particular a heteroarylamine. The term may refer to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, pyridinyl, pyrimidinyl, pyrazinyl, pyridazinyl, triazolyl, tetrazolyl and the like. A heteroaryl group may be optionally substituted with groups disclosed herein, for example with an alkyl, amino, halogen, etc., in particular a substituted heteroaryl group is a heteroarylamine.

The term "heterocyclic" as used herein refers to saturated and partially saturated heteroatom containing ring-shaped groups having at least one heteroatom selected from carbon, nitrogen, sulfur and oxygen. A heterocyclic group may contain one, two or three rings wherein such rings may be attached in a pendant manner or may be fused. In an aspect, the term refers to a saturated and partially saturated heteroatom-containing ring-shaped groups having from about 3 to 15, 3 to 10, 5 to 15, 5 to 10, or 3 to 8 ring members selected from carbon, nitrogen, sulfur and oxygen, wherein at least one ring atom is a heteroatom. Exemplary saturated heterocyclic groups include without limitation a saturated 3 to 6-membered heteromonocylic group containing 1 to 4 nitrogen atoms [e.g. pyrrolidinyl, imidazolidinyl, and piperazinyl]; a saturated 3 to 6-membered heteromonocyclic group containing 1 to 2 oxygen atoms and 1 to 3 nitrogen atoms [e.g. morpholinyl; sydnonyl]; and, a saturated 3 to 6-membered heteromonocyclic group containing 1 to 2 sulfur atoms and 1 to 3 nitrogen atoms [e.g., thiazolidinyl] etc. Examples of partially saturated heterocyclyl groups include without limitation dihydrothiophene, dihydropyranyl, dihydrofuranyl and dihydrothiazolyl. Illustrative heterocyclic groups include without limitation aziridinyl, azetidinyl, 2-pyrrolinyl, 3-pyrrolinyl, pyrrolidinyl, azepinyl, 1,3-dioxolanyl, 211-pyranyl, 4H-pyranyl, piperidinyl, 1,4-dioxanyl, morpholinyl, pyrazolinyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, quinuelidinyl, quinolizinyl, and the like.

The term "hydroxyalkyl" as used herein refers to an alkyl group substituted with an —OH group.

The term "hydroxyl" as used herein refers to the —OH group.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The terms "fluorescence quencher", "quencher", or "quenching moiety" as used herein refer to a molecule that interferes with the fluorescence emitted by a fluorophore or bioluminescent polypeptide. This quencher can be selected from non-fluorescent aromatic molecules, to avoid parasitic emissions. Exemplary quenchers include, but are not limited to, Dabsyl or a BLACK HOLE QUENCHER® that are non-fluorescent aromatic molecules that prevent the emission of fluorescence when they are physically near a fluorophore. The quencher can also be, but is not limited to, a fluorescent molecule, for example TAMRA (carboxytetramethylrhodamine). A particularly advantageous quencher suitable for use in the compositions of the disclosure is a modified dye such as IR-775-COOH. When the quencher is a fluorescent dye, its fluorescence wavelength is typically substantially different from that of the reporter dye.

The term "fluorophore" as used herein refers to any reporter group whose presence can be detected by its light emitting properties.

The term "imaging agent" as used herein refers to a labeling moiety that is useful for providing an indication of the position of the label and adherents thereto, in a cell or tissue of an animal or human subject, or a cell or tissue under in vitro conditions. Such agents may include those that provide detectable signals such as fluorescence, luminescence, radioactivity, or can be detected by such methods as MRI imaging, PET imaging and the like.

The "imaging moiety" may be detected either externally to a subject human or non-human animal body or via use of detectors designed for use in vivo, such as intravascular radiation or optical detectors such as endoscopes, or radiation detectors designed for intra-operative use. The imaging moiety is preferably chosen from, but is not limited to a positron-emitting radioactive non-metal or a reporter suitable for in vivo optical imaging. It is contemplated, however, that other detectable labels may be incorporated into the probes of the disclosure including, but not limited to a radioactive nuclide. When the imaging moiety is a radioactive metal ion, i.e. a radiometal, suitable radiometals can be either positron emitters such as $^{64}$Cu, $^{48}$V, $^{52}$Fe, $^{55}$Co, $^{94}$mTc or $^{68}$Ga or γ-emitters such as 99mTc, $^{111}$In, $^{113}$In, $^{67}$Ga. When the imaging moiety is a positron-emitting radioactive non-metal, suitable such positron emitters can include: $^{11}$C, $^{13}$N, $^{15}$O, $^{17}$F, $^{18}$F, $^{75}$Br, $^{76}$Br or $^{124}$I.

The term "detectable moiety" as used herein refers to a label molecule (isotopic or non-isotopic) which is incorporated indirectly or directly into a liposomal nanoparticle according to the disclosure, wherein the label molecule facilitates the detection of the nanoparticle in which it is incorporated. Thus, "detectable moiety" is used synonymously with "label molecule". Label molecules, known to those skilled in the art as being useful for detection, include chemiluminescent or fluorescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

Spectroscopic, photochemical, biochemical, immunochemical, electrical, optical or chemical means can be used to detect such labels. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis.

The term "label" or "tag" as used herein refers to a molecule that, when appended by, for example, without limitation, covalent bonding or hybridization to another moiety, for example, also without limitation, a nanoparticle provides or enhances a means of detecting the other moiety. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal-generation detection methods include: chemiluminescence, electrochemiluminescence, raman, colorimetric, hybridization protection assay, and mass spectrometry. Radionuclides may be either therapeutic or diagnostic; diagnostic imaging using such nuclides is also well known. Typical diagnostic radionuclides include, but are not limited to, $^{99}$Tc, $^{95}$Tc, $^{111}$In, $^{62}$Cu, $^{64}$Cu, $^{67}$Ga, $^{68}$Ga.

The term "lower-alkyl-substituted-amino" as used herein refers to any alkyl unit containing up to and including eight carbon atoms where one of the aliphatic hydrogen atoms is replaced by The term "lower-alkyl-substituted-halogen" as used herein refers to any alkyl chain containing up to and including eight carbon atoms where one of the aliphatic hydrogen atoms is replaced by a halogen. Examples of such include, but are not limited to, chlorethyl and the like.

The term "Magnetic Resonance Imaging" or (MRI) as used herein is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

The term "modulated detectable signal" as used herein refers to a detectable signal emitted by a label moiety that is reduced in intensity or otherwise changed such as, but not limited to, a change in wavelength such that the modulated signal is detectably distinct from a unmodulated signal. A modulated signal can be, for example, a quenched signal where some or all of the energy of the unmodulated signal is absorbed by a second label moiety so that the modulated signal is less intense than the original signal. Alternatively, for example, a first signal from a first label moiety may be a stimulant for a second label moiety to emit a signal of a different wavelength.

The term "nitro" as used herein means —NO$_2$—.

The term "operably linked" as used herein refers to an arrangement of elements wherein the components so described are configured so as to perform their usual function.

The term "oxo" as used herein refers to a compound described previously herein wherein a carbon atom is replaced by an oxygen atom.

The term "pendant" as used herein refers to a chemical substituent "pendant" from a group if it is bound to an atom of the group. In this context, the substituent can be pending from a carbon atom of a group, a carbon atom connected to a carbon atom of the group by a chain extender, or a heteroatom of the group. The term "fused" means that a second ring is present (i.e., attached or formed) by having two adjacent atoms in common or shared with the first ring.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The compounds of the disclosure may also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M, Berge, at al., J. Pharmaceutical Sciences, 1977, 66:1. Suitable salts include salts that may be formed where acidic protons in the compounds are capable of reacting with inorganic or organic bases. Suitable inorganic salts include those formed with alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Suitable salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

The term "pure" as used herein refers to better than 90%, 92%, 93%, 94%, 95%, 96%, 97%, 98% or 99% pure, and "substantially pure" means a compound synthesized such that the compound, as made or as available for consideration into a composition or therapeutic dosage described herein, has only those impurities that cannot readily nor reasonably be removed by conventional purification processes.

The term "phosphonate" refers to a C—PO(OH)$_2$ or C—PO(OR$_{27}$)$_2$ group wherein R$_{27}$ is alkyl or aryl which may be substituted.

The term "positron emission tomography" as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 (about 20 min), nitrogen-13 (about 10 min), oxygen-15 (about 2 min), and fluorine-18 (about 110 min). PET technology can be used to trace the biologic pathway of any compound in living humans (and many other species as well), provided it can be radiolabeled with a PET isotope. The half-life of fluorine-18 is long enough such that fluorine-18 labeled radiotracers can be manufactured commercially at an offsite location.

The terms "quench" or "quenches" or "quenching" or "quenched" as used herein refer to reducing the signal produced by a molecule. It includes, but is not limited to, reducing the signal produced to zero or to below a detectable limit. Hence, a given molecule can be "quenched" by another molecule and still produce a detectable signal albeit the signal is greatly reduced.

The terms "fluorescence quencher" or "quencher" as used herein refers to molecules that interfere with or absorb the fluorescence emitted by a nearby fluorophore. Exemplary quenchers include, but are not limited to, Dabsyl or a Black hole Quencher® that are non-fluorescent aromatic molecules. A quencher can also be a second fluorescent molecule, for example TAMRA (carboxytetramethylrhodamine) that emits at a different wavelength.

The term "selectively cleavable" as used herein refers to when a linker is not cleaved by certain reactions conditions, but selectively cleavable by different reaction conditions. The selectively cleavable peptide of the probes of the disclosure will include a peptide bond that can be cleaved by peptidase the activity of which is to be detected by the probe, but not cleaved by other peptidases.

The term "self-immolative probe" as used herein refers to a signaling molecule covalently bound to a moiety (a "self-immolative arm" or "self-immolative linker") such that the self-immolative arm inhibits the signaling molecule from signaling. The self immolative arm is covalently bound to an reporter moiety such as a fluorophore of the disclosure such that the removal of a moiety by the action of an enzyme, for example, causes a destabilization of the self-immolative arm such that the self immolative arm becomes removed from the signaling molecule, allowing the signaling molecule to signal. The "self-immolative" moieties of the disclosure include such as a substrate group of an enzyme. For example, but not intended to be limiting a self-immolative linker may have attached thereon a phosphate group. A cellular phosphatase may, on contact with a probe of the disclosure, cleave the phosphate group from the linker, thereby allowing the liner to reconfigure to allow electron transfer to the fluorophore to emit a detectable signal.

The term "specific binding" as used herein refers to the specific recognition of one molecule, of two different molecules, compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

The terms "subject" and "patient" as used herein include humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. In some embodiments, a system includes a sample and a subject. The term "living host" refers to host or organisms noted above that are alive and are not dead. The term "living host" refers to the entire host or organism and not just a part excised (e.g., a liver or other organ) from the living host.

The term "substituted alkenyl" as used herein includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

In aspects of the disclosure, "substituted alkyl" includes an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthio, arylthio, aralkylthio, sulfonamide, thioalkoxy; and nitro.

The term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "substituted aryl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic), alkylamino, dialkylamino, sulfate, and mercapto Examples of such include, but are not limited to, hydroxyphenyl, chlorphenyl and the like.

The term "substituted cycloaliphatic" as used herein refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

The term "substituted cycloalkyl" as used herein includes cycloalkyl groups having from 1 to 5 (in particular 1 to 3) substituents including without limitation alkyl, alkenyl, alkoxy, cycloalkyl, substituted cycloalkyl, acyl, acylamino, acyloxy, amino, aminoacyl, aminoacyloxy, oxyacylamino, cyano, halogen, hydroxyl, carboxyl, carboxylalkyl, keto, thioketo, thiol, thioalkoxy, aryl, aryloxy, heteroaryl, heteroaryloxy, hydroxyamino, alkoxyamino, and nitro.

The term "substituted heterocyclic" as used herein refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amid; a lower aliphatic, a substituted lower aliphatic, or a ring (aryl, substituted aryl, cycloaliphatic, or substituted cycloaliphatic). Examples of such groups include, but are not limited to 2-chloropyranyl.

The term "sulfate" as used herein refers to the $-SO_4$ group.

The term "sulfenyl" as used herein used alone or linked to other terms such as alkylsulfenyl, refers to the group $-SR$ wherein R is not hydrogen. In aspects of the disclosure R is substituted or unsubstituted alkyl, cycloalkyl, alkenyl, alkynyl, aryl, silyl, silylalkyl, heterocyclic, heteroaryl, carbonyl, carbamoyl, alkoxy, or carboxyl.

The term "sulfonyl" as used herein used alone or linked to other terms such as alkylsulfonyl or arylsulfonyl, refers to the divalent groups $-SO_2^-$. In aspects of the disclosure, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "sulfoxide" refers to the group $-S=O$.

The term "substituted aliphatic" as used herein refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

The term "sulfinyl" as used herein, used alone or linked to other terms such as alkylsulfinyl (i.e. $-S(O)$-alkyl) or arylsulfinyl, refers to the divalent groups $-S(O)-$.

The term "thio" as used herein refers to a compound described previously herein wherein a carbon or oxygen atom is replaced by a sulfur atom.

The term "thioalkoxy" as used herein, alone or in combination, refers to a chemical functional group where a sulfur atom (S) is bonded to an alkoxy group with the general chemical formula $-SR_{24}$ where $R_{24}$ is an alkoxy group which may be substituted. A "thioalkoxy group" may have 1-6 carbon atoms i.e. a $-S-(O)-C_1-C_6$ alkyl group wherein $C_1-C_6$ alkyl have the meaning as defined above. Illustrative examples of a straight or branched thioalkoxy group or group having from 1 to 6 carbon atoms, also known as a $C_1-C_6$ thioalkoxy, include thiomethoxy and thioethoxy.

The term "thioalkyl" as used herein, alone or in combination, refers to a chemical functional group where a sulfur atom (5) is bonded to an alkyl, which may be substituted. Examples of thioalkyl groups are thiomethyl, thioethyl, and thiopropyl. A thioalkyl may be substituted with a substituted or unsubstituted carboxyl, aryl, heterocylic, carbonyl, or heterocyclic.

The term "thioaryl" as used herein, alone or in combination, refers to a chemical functional group where a sulfur atom (S) is bonded to an aryl group with the general chemical formula $-SR_{23}$ where $R_{23}$ is aryl which may be substituted. Illustrative examples of thioaryl groups and substituted thioaryl groups are thiophenyl, chlorothiophenol, para-chlorothiophenol, thiobenzyl, 4-methoxy-thiophenyl, 4-nitro-thiophenyl, and para-nitrothiobenzyl.

The term "thiol" as used herein means $-SH$. A thiol may be substituted with a substituent disclosed herein, in particular alkyl (thioalkyl), aryl (thioaiyl), alkoxy (thioalkoxy) or carboxyl. A thiol may be substituted with a substituted or unsubstituted heteroaryl or heterocyclic, in particular a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydrionyl], especially a substituted morpholinyl or piperidinyl.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Discussion

A major limitation to current chemiluminescent and bioluminescent probes is the emission of light with extremely short lifetimes and short wavelengths (i.e., less than 650 nm), which prohibits the use of the probes for high-throughput analyses and deep tissue imaging. Accordingly, the present disclosure encompasses embodiments of a multi-modal probe that combines near-infrared (NIR) chemiluminescent emission (i.e., greater than 650 nm) with positron emission tomography (PET) to provide high contrast imaging of upregulated enzymatic activity. Also encompassed by the present disclosure are multi-modal imaging probes that can use, for example, enzyme-triggered activation of chemiluminescent 1,2-dioxetanes for generating the emission of NIR light, and the accumulation of a radiolabel ($^{18}F$) for the purpose of imaging such as a furin activity in glioblastoma.

The present disclosure encompasses embodiments of a novel fluorophore useful to image biological structures and functions in vitro and in vivo. There are a few NIR molecular dyes currently available and most suffer from one or more of the following drawbacks: poor water-solubility, low fluorescence emission, difficult chemical modification, and/or charged functional groups that cause the dyes to localize to undesired cellular compartments (e.g., mitochondria, lysosomes, etc.). The rhodol fluorophores of the disclosure improve upon existing fluorophores in the following ways: (a) they are relatively water soluble due to its small size and nitrogen/oxygen hydrogen bond acceptors which promote solvation by water molecules. In contrast, cyanine dyes, for example, tend to aggregate in water and react nonspecifically with biomolecules, which complicates in vivo usage; (b) they have a very large Stokes shift (greater than 100 nm) which is considerably longer than typical NIR fluorophores (20-40 nm); (c) they are pH-insensitive and robust to changing external environments compared to the following structurally similar and competing NIR fluorophores. Thus, fluorescein, for example, is highly sensitive to pH, especially in the physiological range (pKa=6.3) and rhodamines (e.g., Rhodamine B, Rhodamine 123, etc.) are also pH-sensitive; (d) the core structure is uncharged, which facilitates cell penetration without localization. Rhodamines, in contrast, are positively-charged and as a result, tends to localize to mitochondria and lysosomes; and (e) the rhodol is simple to synthesize and can be readily modified through one-step chemical reactions.

In embodiments of the rhodol fluorophores of the disclosure, substituents are possible at the $R_1$ position (as shown in FIG. 1). This position is a key place to append functional groups that undergo bioorthogonal reactions to "tag" molecules or structures of interest (e.g., acetylene, amine, carboxylic acid, etc.). It is also possible append aryl groups to this position to modify the fluorescence properties of the fluorophore (e.g., thiophene). Alternative groups include, but are not limited to, alkyl, aryl, alkoxy, aryloxy, carbonyl, sulfonyl, phosphoryl, azido, amino, amido, and nitro. It is further possible to introduce substituents at the $R_2$ and $R_3$ such as, for example, H, alkyl, alkoxy, aryl, aryloxy, azido, amino, amido, carbonyl, sulfonyl, or phosphoryl and also to pegylate the fluorophore at at least one of the positions $R_2$ and $R_3$.

Accordingly, the present disclosure provides novel rhodol fluorophores and derivatives thereof that have a tetrahydroquinoxaline (THQ) framework. They are useful in activatable probes, are biocompatible, functionalizable NIR fluorophores with Stokes shifts greater than 200 nm. The fluorophores of the disclosure satisfy a long-felt need for an expanded repertoire of fluorescent dyes for diagnostic and biomedical applications. For example, the field of fluorescence image-guided surgery has become increasingly popular. The development of robust NIR dyes, tags, and probes is necessary to furthering advancements in this field.

There are many imaging modalities available for in vitro and preclinical in vivo imaging (e.g., PET, CT, MRI, X-ray). However, many of these modalities are cost-prohibitive and/or expose the biological sample or specimen to damaging ionizing radiation. Small NIR fluorescent molecules such as the fluorophores of the present disclosure are inexpensive to make, non-invasive, do not require ionizing radiation, and can be made to target specific biomarkers to gain specificity. They can provide greater detail in structural and functional information through coupling to other imaging modalities, can be activatable which means they turn "on" only upon a desired biological event thereby providing lower background signals compared to other contrast agents and tracers which are always "on."

Accordingly, the disclosure further provides novel molecular constructs that include a THQ-based rhodol fluorophore of the disclosure and which allow for multimodality imaging of biological activities in a research, preclinical, or clinical setting. The fluorophore is versatile because it can be used as a dye, fluorescent tag, or as an optical reporter when serving as a molecular probe or sensor. As a tag, the fluorophore can be tailored to attach to or recognize other molecular constructs or biomolecules via convenient handles using standard bioorthogonal chemistries. The multi-modal probes provided combines near-infrared (NIR) chemiluminescent emission (i.e., greater than 650 nm) with additional detectable labeling moieties that allow for the detection of the probe by such means as positron emission tomography (PET). Also encompassed by the present disclosure are multi-modal imaging probes that can use enzyme-triggered activation of chemiluminescent 1,2-dioxetanes for generating the emission of NIR light. Such probe constructs allow for the detection of an enzyme activity and an accumulation of a radiolabel such as $^{18}F$ permits the imaging of the enzyme activity within a tissue. Thus, the fluorophore probe of the disclosure, for example, may include a furin-specific peptide for the detection of furin activity in glioblastoma.

As a probe, the response of the fluorophore can be modulated between an "off" and "on" fluorescence state. The design, chemical, and spectral/photophysical properties of the fluorophore are well-suited for use in the development of multimodal imaging tools in in vitro, ex vivo, and in vivo analyses because these elements allow for an activatable near-infrared (NIR) fluorescence response as well as provide the ability to reversibly or to irreversibly bioconjugate the fluorophore to either sites of interest or other delivery vehicles. In addition, the fluorophore demonstrates an approximate 200 nm Stokes shift in aqueous conditions and displays no net charge, which allows for cell membrane penetration without the unintended effect of localizing to particular cellular compartments (common to commercially available fluorophores).

Existing NIR Dyes:

The optical imaging window for visualizing biological activities or structures is between 650-900 nm because the absorption and emission wavelengths within this range provide minimal native background, low tissue absorption (i.e., scattering), deeper tissue penetration, and little photochemical damage in living systems. One of the most common classes of NIR fluorophores used for in vivo imaging is the cyanine class of dyes (e.g., Cy5 and IR-780). However, this class of dyes has suboptimal properties. They are prone to photobleaching, oxidation, solvatochromic effects, and nonspecific interactions with plasma proteins. Moreover, cyanine dyes have low quantum yields due to competitive internal conversion and photoisomerization as well as display an inherent net charge that causes localization to specific cellular compartments. To address these shortcomings, additional classes of NIR dyes have been developed that are based on other unique scaffolds such as the phthalocyanine, xanthene, boron dipyrromethane (BODIPY), benzo[c]heterocycle, porphyrin, and squaraine platforms. However, these classes of fluorophores either demonstrate poor water solubility, cannot permeate the cell membrane, or afford a narrow Stokes shift (i.e., less than 40 nm).

The development of NIR dyes that can be utilized for in vivo imaging remains a challenge. Currently, there are only a limited number of FDA clinically approved fluorophores that can be used for in vivo imaging applications (e.g., fluorescein, methylene blue, and indocyanine green). As a result, there is a pressing need for fluorophores that demonstrate excellent chemical/photochemical stability, high quantum yields, large Stokes shifts, emit in the NIR spectral region, and can be tailored to specific applications in a facile manner. The NIR-emitting rhodol fluorophores of the disclosure are based on a 1,2,3,4-tetrahydroquinoxaline (THQ) framework that can be prepared in five simple steps, which permits easy chemical modification at key sites on the structure. The rhodol fluorophore emits at 711 nm under aqueous conditions and displays a Stokes shift that is approximate 200 nm. The large Stokes shift is a highly desirable property because the rhodol fluorophore can be used concurrently with other fluorophores that can be excited at the same wavelength, thereby resulting in two distinct emission wavelengths that can afford quantitative analysis of biological activity or biomolecules.

Figure 1B:
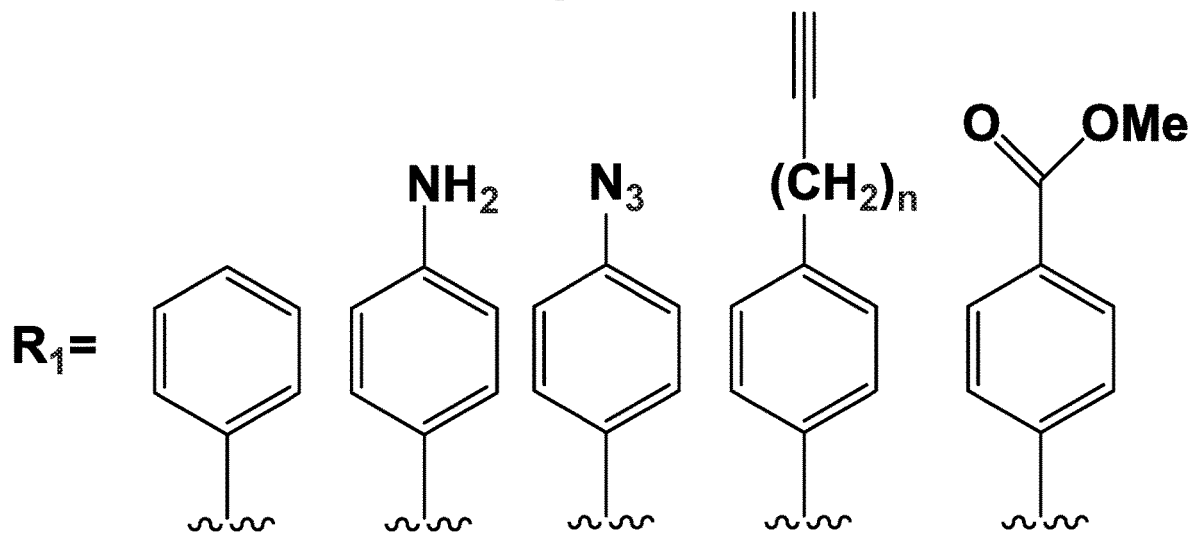
FIG. 1B illustrates representative embodiments of the THQ-based rhodol fluorophore of the disclosure serving as a Near Infra-Red (NIR)-emitting fluorescent tag for biomolecules. Several groups can be appended off of the fluorophore to allow them to be easily fixed to structures of interest through bioorthogonal chemistries.

Structure & Synthesis:

The structure of the THQ rhodol fluorophore is shown in FIG. 1A, where the scaffold resembles a hybrid of the scaffold of both fluorescein and rhodamine, two common fluorophores (FIG. 1A). The rhodol fluorophores of the disclosure possess, in part, a xanthene backbone where C2 and C3 have nitrogen substituents that are fused together in a ring. C9 possesses a substituent that can be alkyl, alkenyl, alkynyl, alkoxy, aryl, aryloxy, heteroaryl, cyano, azido, nitro, amino, amido, carbonyl, sulfonyl, phosphoryl, halogen, or other heteroatom. Aliphatic and aromatic substituents can be appended to the C9 position (e.g., a benzene moiety that can be further functionalized at any of the positions C11-15 (substituents $R_{11}$-$R_{15}$) that can either modify the fluorescence output or provide a handle to attach (reversibly or irreversibly) the fluorophore to other molecules or structures of interest. Some non-limiting examples of $R_1$ variants are illustrated in FIG. 1B.

Unlike fluorescein and rhodamine, the rhodol structures of the present disclosure are not pH-sensitive, thereby affording a response that does not fluctuate with any changes in the biological environment (e.g., pH value). Moreover, the THQ-based rhodol fluorophore exhibits a very large Stokes shifts (about 200 nm) compared to most fluorophores (20-40 nm) and is fully soluble in aqueous conditions. Due to its excellent photophysical properties in water and the ease toward synthetic modification, the rhodol fluorophores of the disclosure are useful, for example, as a fluorescent dye, a fluorescent tag, or as an activatable molecular probe or sensor.

Figure 2:
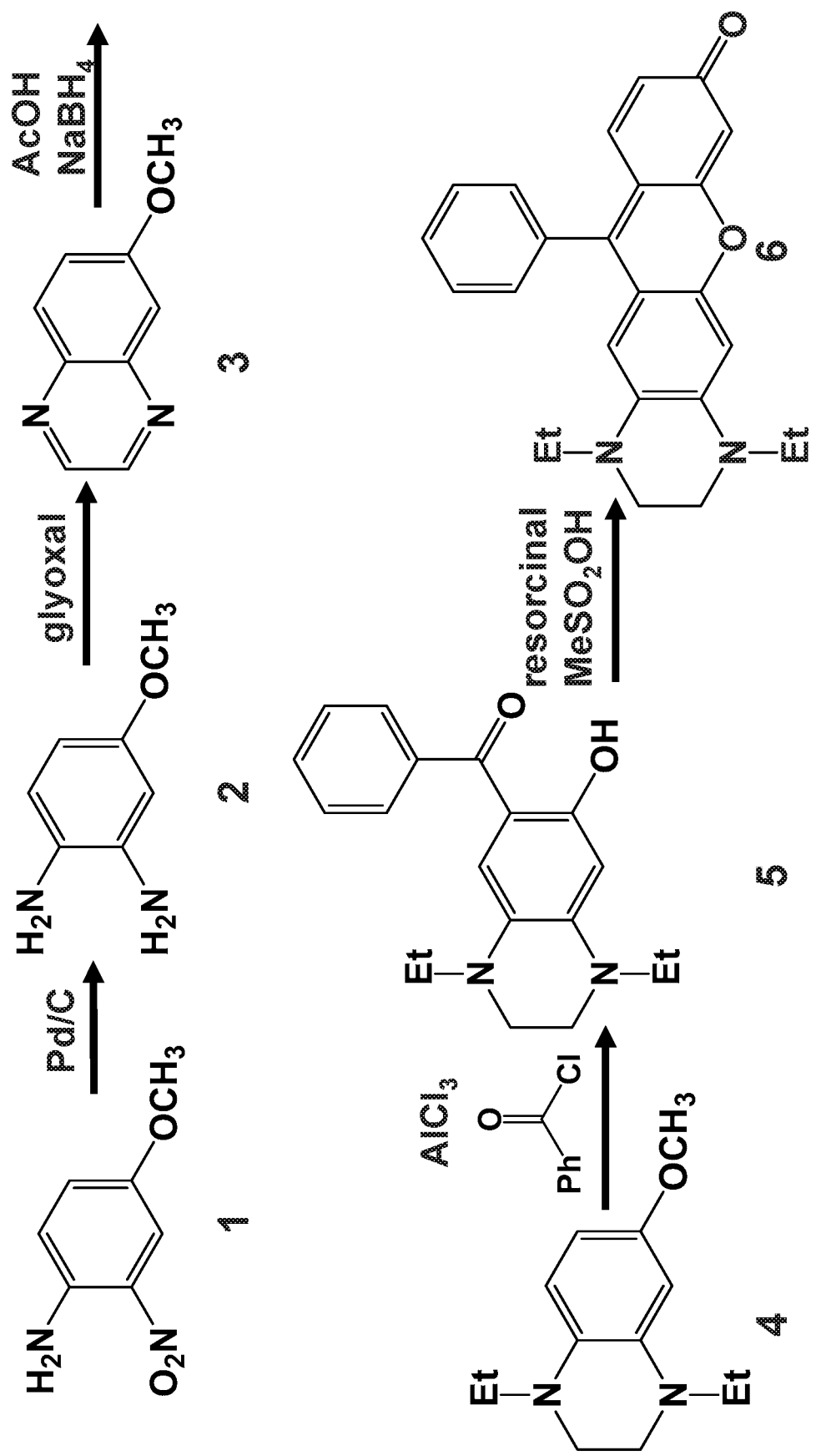
FIG. 2 illustrates a representative synthetic scheme for the development of an embodiment of an NIR-emitting fluorescent rhodol dye (6).

The standard synthesis of a rhodol fluorophore can be achieved from commercially available starting materials in five steps or from known compound 4 in two steps, as shown in FIG. 2. A variety of acyl chlorides can be used in the fourth reaction to easily modify the substituent at the C9 (i.e. $R_1$). For example, a thiophene can be append to the 9-position which can increase the absorption and fluorescence emission wavelengths by an additional 15 nm.

Accordingly, one aspect of the disclosure encompasses embodiments of a compound having the formula (I):

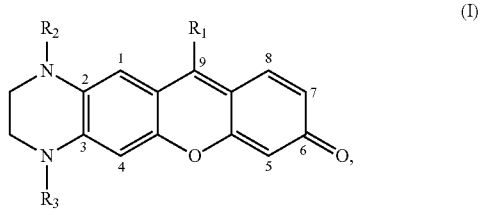

(I)

wherein: $R_2$ and $R_3$ can be independently H, an alkyl, an alkenyl, an alkynyl, an alkoxy, an aryl, an aryloxy, a heteroaryl, a cyano, an azido, a nitro, an amino, an amido, a carbonyl, a sulfonyl, a phosphoryl, a halogen, a heteroatom, a polyethylene glycol (PEG), or a self-immolative linker, and wherein the self-immolative linker can be conjugated to any of a fluorescence quencher, a chemiluminescent emitter, an MRI contrast agent, or a cell-penetrating peptide, and $R_1$ can be H, an alkyl, an alkenyl, an alkynyl, an alkoxy, an aryl, a substituted aryl, an aryloxy, a heteroaryl, a cyano, an azido, a nitro, an amino, an amido, a carbonyl, a sulfonyl, a phosphoryl, a halogen, a heteroatom, a fluorescence quencher, or a chemiluminescent emitter.

In some embodiments of this aspect of the disclosure, the self-immolative linker can be conjugated to a caging moiety.

In some embodiments of this aspect of the disclosure, the caging moiety is a cleavable enzyme substrate, wherein the cleavable substrate is attached to the self-immolative linker in a position that prevents the emission of a detectable signal from the compound.

In some embodiments of this aspect of the disclosure, the cleavable enzyme substrate ca be a peptide conjugated to the self-immolative linker by a protease.

In some embodiments of this aspect of the disclosure, the protease can be furin.

In some embodiments of this aspect of the disclosure, the cleavable substrate is a phosphate group, an amino group, an alkyl group, a hydroxyl group, a carboxyl group, an amino acid, or a peptide.

In some embodiments of this aspect of the disclosure, the self-immolative linker can be conjugated to a metal chelator and the further comprises a detectable metal ion.

In some embodiments of this aspect of the disclosure, the detectable metal ion can be gadolinium.

In some embodiments of this aspect of the disclosure, the peptide can have the amino acid sequence Arginine-Arginine-Valine-Arginine (RRVR) and be cleavable from the compound by furin.

In some embodiments of this aspect of the disclosure, $R_1$ can be an aryl or a substituted aryl having the formula (II):

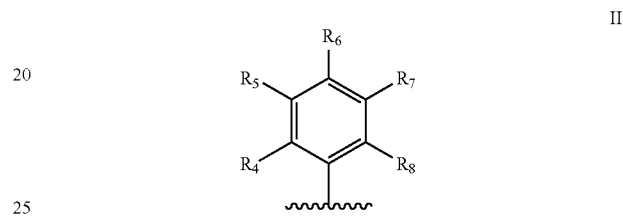

II wherein $R_4$-$R_8$ can be independently H, an alkyl, an alkenyl, an alkynyl, an alkoxy, an aryl, an aryloxy, a heteroaryl, a cyano, an azido, a nitro, an amino, an amido, a carbonyl, a sulfonyl, a phosphoryl, a halogen, a heteroatom, a self-immolative linker, or a self-immolative linker conjugated to a fluorescence quencher, a chemiluminescent emitter, or an MRI contrast agent. In some of these embodiments of the aspect of the disclosure, $R_4$-$R_5$ and $R_7$-$R_8$ can be each H and $R_6$ is an alkynyl group, an alkoxy group, an azido group, or an amino group.

In some embodiments of this aspect of the disclosure, the compound can have the formula (III) or (IV)

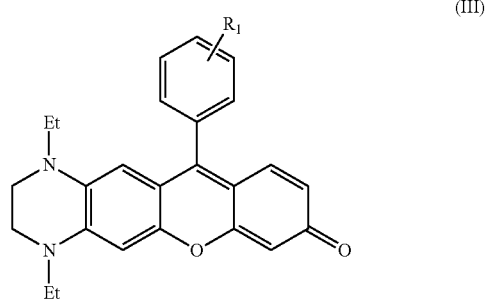

(III)

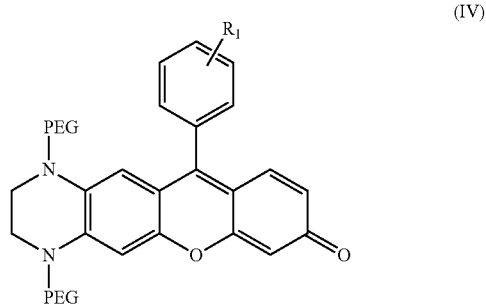

(IV)

wherein $R_1$ can be an amine, a substituted amine, an azide group, an alkyne, or an acetyl group.

In some embodiments of this aspect of the disclosure, $R_1$ can be selected from —$NH_2$, —$N_3$, —$(CH_2)_nC\equiv C$, or —COOMe.

Another aspect of the disclosure encompasses embodiments of a multimodality probe comprising an embodiment of any of the above compounds of the disclosure.

In some embodiments of this aspect of the disclosure, said probe can be selected from the formula A, B, C, D:

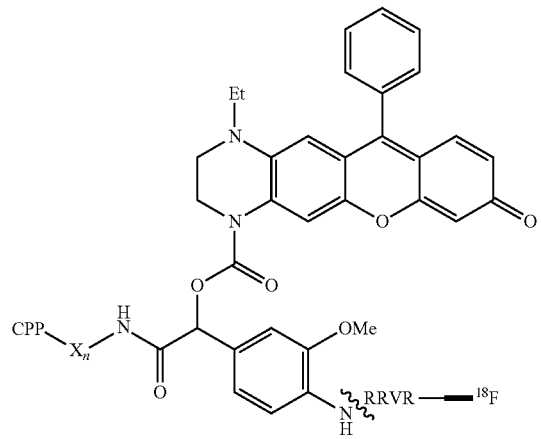

Another aspect of the disclosure encompasses embodiments of a composition comprising an embodiment of any of the above compounds of the disclosure.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

Example 1

Use as a Fluorescent Tag:

The NIR rhodol can be used as a tag to identify structures or analytes of interest (e.g., biomolecules). As a tag, the fluorescence remains "on". As shown in the fourth reaction in FIG. 2, various acyl chloride reagents can be used to append a variety of substituents at the 9-position using a standard Friedel-Crafts acylation mechanism in order to introduce handles that are commonly used for bioconjugation and/or bioorthogonal ligation reactions (e.g., Staudinger ligation, inverse Diels-Alder reactions, oxime and hydrazone formation, aminothiol-CBT condensations, alkyne-azide Click chemistry, and etc.). Shown in FIG. 1B are several variants of the pendant substituent that can be developed to tag or conjugate biomolecules. It is contemplated that other acyl chloride derivatives can also be used in the probes of the disclosure, thereby expanding the repertoire of tagged and conjugate probes.

Example 2

Use as a Molecular Probe:

The NIR rhodol fluorophore can be utilized as part of an activatable molecular probe or sensor. In a representative example, the rhodol would be in an "off" fluorescence state until a specific event occurs (e.g., presence of a substrate, enzymatic cleavage, interaction with a biomolecule, and etc.), which transforms the fluorophore to an "on" fluorescence state. There are many benefits to activatable probes, especially in studies that do not allow for a washing step (e.g., in whole body animals), which is a common strategy to help facilitate the removal of any residual dye that could otherwise contribute to the observed fluorescence response (i.e., background signal) when the fluorophore is part of a non-activatable probe. There are several signal transduction mechanisms that can be used to turn the fluorescence from an "off" to "on" state which includes intramolecular charge transfer (ICT), photoinduced electron transfer (PeT), and several variations of Förster resonance energy transfer (FRET).

Examples of the rhodol fluorophore undergoing these aforementioned mechanisms when serving as a probe are provided, as shown in FIGS. 5-7, 9B, 10B, 11B, 12B, 13B, 14B, and 15B. In addition, examples of the rhodol fluorophore incorporating additional imaging modalities are provided. Potential imaging strategies that the NIR rhodol fluorophore can accommodate include one or more of the following modalities: positron emission tomography (PET), magnetic resonance imaging (MRI), computed tomography (CT), and ultrasound.

Example 3

Figure 4:
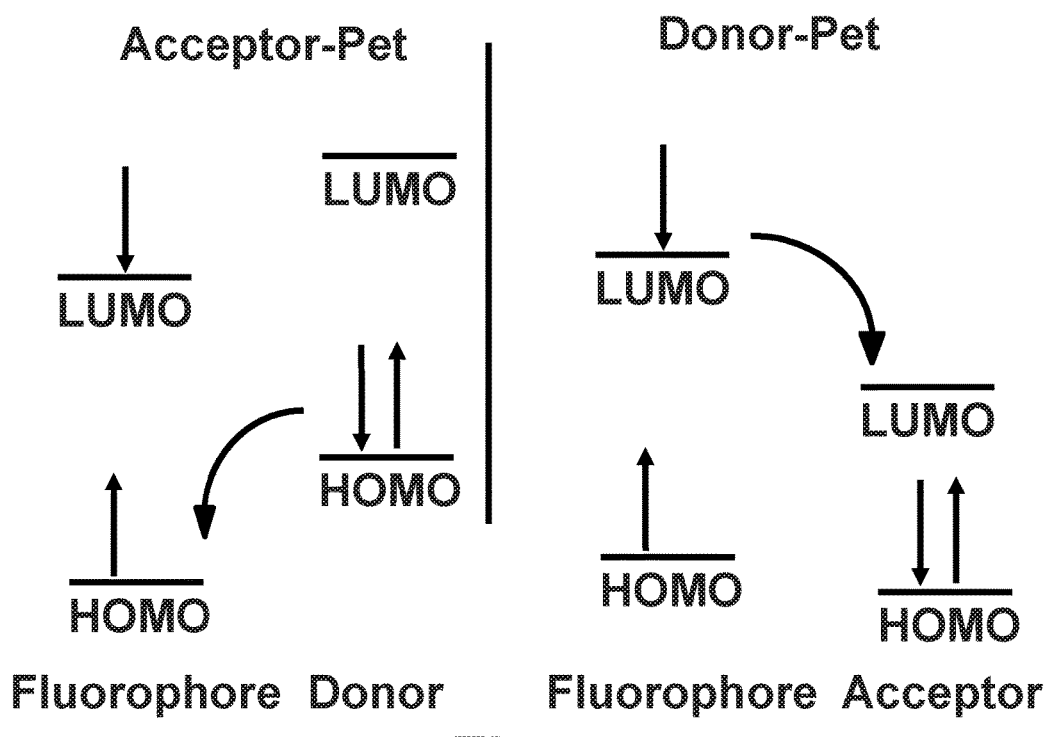
FIG. 4 illustrates two forms of PeT quenching. Acceptor-PeT is when the fluorophore acts as an electron acceptor. Donor-PeT is when the fluorophore acts as an electron donor.

Use as a NIR Fluorescence (ICT):

Rhodol fluorophores of the disclosure can fluoresce through an ICT mechanism, as shown in FIG. 4. The fluorophore possesses an electron-donating group (nitrogen) on one end of the pi-system and an electron acceptor (ketone) on the opposite end of the pi-system. The stronger the electron donor and electron acceptor, the greater is the fluorescence output. In the excited state, the electrons have been delocalized across the fluorophore to create a zwitterion. This resonance structure is particularly stabilized by the dipoles of water molecules which results in increased fluorescence output. This mechanism of activation is advantageous for biological applications as it would be more fluorescent in aqueous conditions than in organic solvents.

Figure 3:
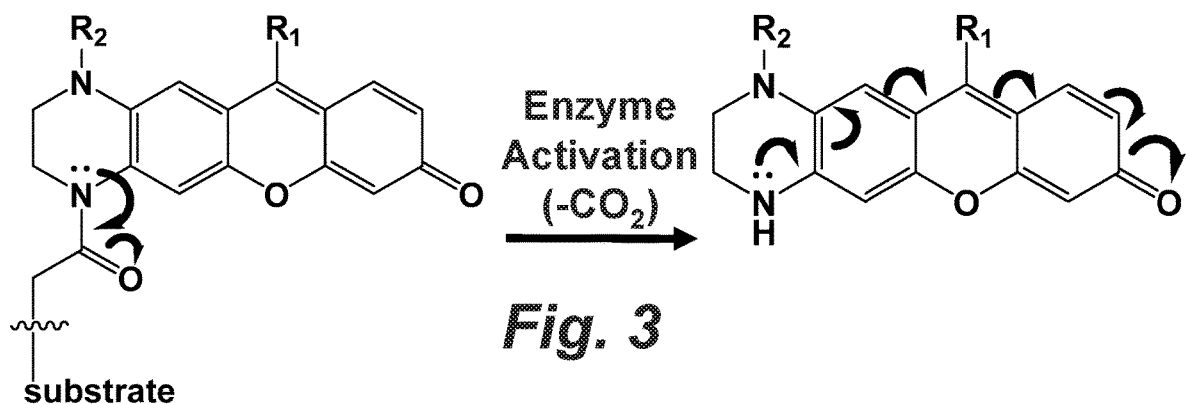
FIG. 3 illustrates the activation of rhodol probe by increasing the intramolecular charge transfer (ICT).

One way to shut down the ICT would be to occupy the donor's electrons so it cannot donate into the pi-system. As shown in FIG. 3, the nitrogen donor is in resonance with a pendant carbonyl group and cannot donate across the pi-system of the fluorophore. That makes the ICT very low and the molecule non-fluorescent. Enzymatic cleavage can liberate the nitrogen electrons and produce a strong fluorescence response due to enhanced ICT in the excited state.

Example 4

Use as a NIR Fluorescence (PeT):

PeT is a way to manipulate the fluorescence response of fluorophores and can be accomplished in two ways (as schematically shown in FIG. 4). For acceptor-PeT quenching, the fluorophore acts as an electron-acceptor in the excited state. A pendant donor group donates an electron into the HOMO of the excited fluorophore. The excited electron must now relax via a nonradiative decay pathway (i.e., no fluorescence emission). For donor-PeT quenching, the fluorophore acts as an electron-donor in the excited state. Instead of fluorescing down to the ground state, the excited electron of the fluorophore migrates into the LUMO of a pendant acceptor which also prohibits fluorescence emission.

This strategy has been incorporated into fluorescent sensors and probes by appending to the fluorophore a PeT quencher that can be released to give a turn-on fluorescence response.

Figure 9A:
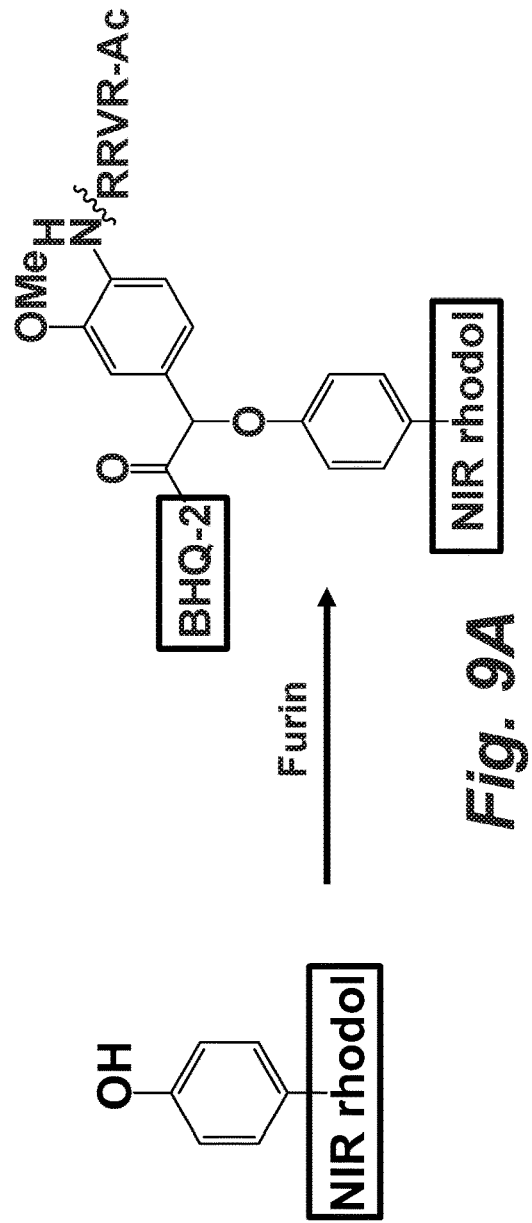
FIG. 9A illustrates an embodiment of a furin-activated NIR-emitting rhodol probe.
Figure 9B:
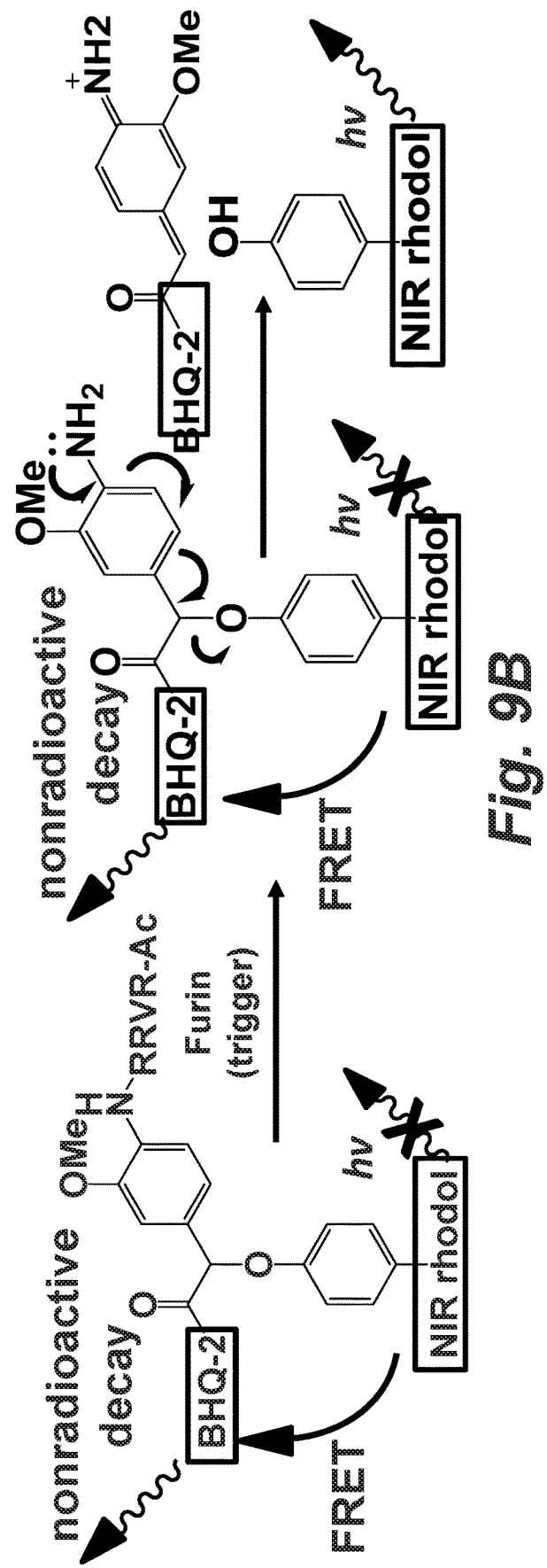
FIG. 9B illustrates an example of an activatable fluorescent probe through relief of PeT quenching. The fluorescence of the rhodol fluorophore is quenched by a pendant PeT quencher (BHQ-2). Enzymatic cleavage by furin activates a self-immolative linker that releases the quencher and resulting in a turn-on fluorescence response.

FIG. 9B illustrates an example of how the black hole quencher 2 (BHQ-2) is used to quench the fluorescence of the rhodol fluorophores of the disclosure after enzymatic cleavage release of the furin substrate (RRVR).

Example 5

Use as a NIR Chemiluminescence (CRET):

Chemiluminescent resonance energy transfer (CRET) is a popular method for imaging as it does not require external light excitation to produce an optical signal. Therefore, CRET provides high sensitivity due to affording very low background. CRET probes have two components: a chemiluminescent (CL) emitter and an energy acceptor (usually a fluorophore). The CL emitter is activated by a chemical reaction and undergoes an irreversible decomposition process where light is produced as a byproduct. The emitted light from the CL emitter can be absorbed by a tethered fluorophore which emits at a longer wavelength.

In FIG. 11B is shown an example of the rhodol fluorophore accepting energy from a 1,2-dioxetane CL emitter activated by enzymatic cleavage. Different enzyme substrates could be attached to the phenolic position of the CL emitter making this design universal and easily translated for studies of various disease mechanisms. In FIG. 11B is shown the use of a phosphate group that can be cleaved from the probe by a phosphatase activity. Other suitable substrates include such an amine group removable by a transaminase, an amino acid or a peptide removable by a peptidase.

In lieu of CRET, this strategy may be used with FRET where the CL emitter is replaced with a lower wavelength-emitting fluorophore as shown in FIG. 10B. This would allow to excite the complex repeatedly and to use two separate excitation wavelengths for each of the fluorophores.

Example 6

Figure 5:
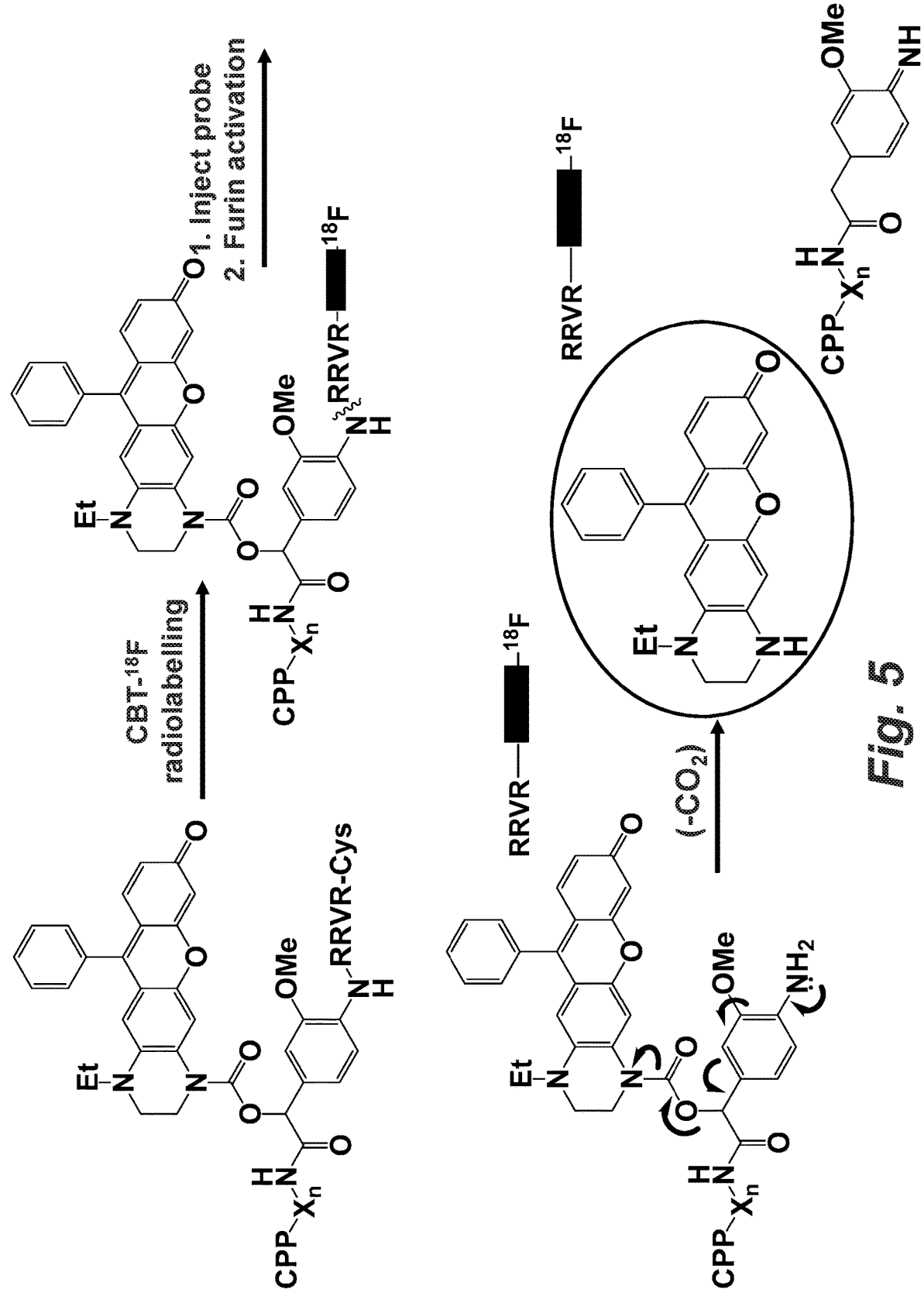
FIG. 5 illustrates a multimodal fluorescence/PET smart probe for specifically detecting furin activity. The probe consists of: a rhodol fluorophore, a self-immolative linker, an enzyme substrate, and a radioactive label. First, the non-fluorescent probe is radiolabeled. Then, the probe is injected into the specimen. It will penetrate the blood-brain barrier (BBB) due to the cell penetrating peptide (CPP) targeting ligand and enter the GBM cell to be cleaved by furin. Enzymatic cleavage activates the self-immolative linker that releases the rhodol fluorophore in its fluorescent form. The cleaved radiolabel is positively charged (due to the arginines) and will stay trapped inside the cell causing accumulation and an increase in the PET signal. The cysteic acids are to balance the charge so the probe is neutral going into the cell. RRVR=Arg-Arg-Val-Arg; X=cysteic acid.

Use as a Multimodal Probe (NIR Fluorescence & PET):

The rhodol fluorophore can be used as part of a larger multimodal imaging device. In FIG. 5 is schematically shown an example of a dual-modal (fluorescence & PET) activatable (a.k.a. "smart") probe for evaluating the enzymatic activity of furin, which is an enzyme upregulated in several human cancers. The PET imaging allows for translation into larger mammals as it is can penetrate deep into tissues.

Example 7

Figure 12A:
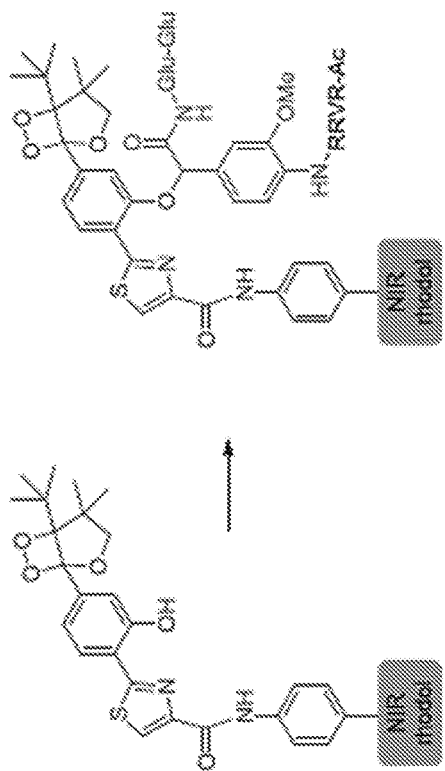
FIG. 12A illustrates an embodiment of a furin-activated NIR-emitting CRET probe incorporating an NIR rhodol of the disclosure.
Figure 12B:
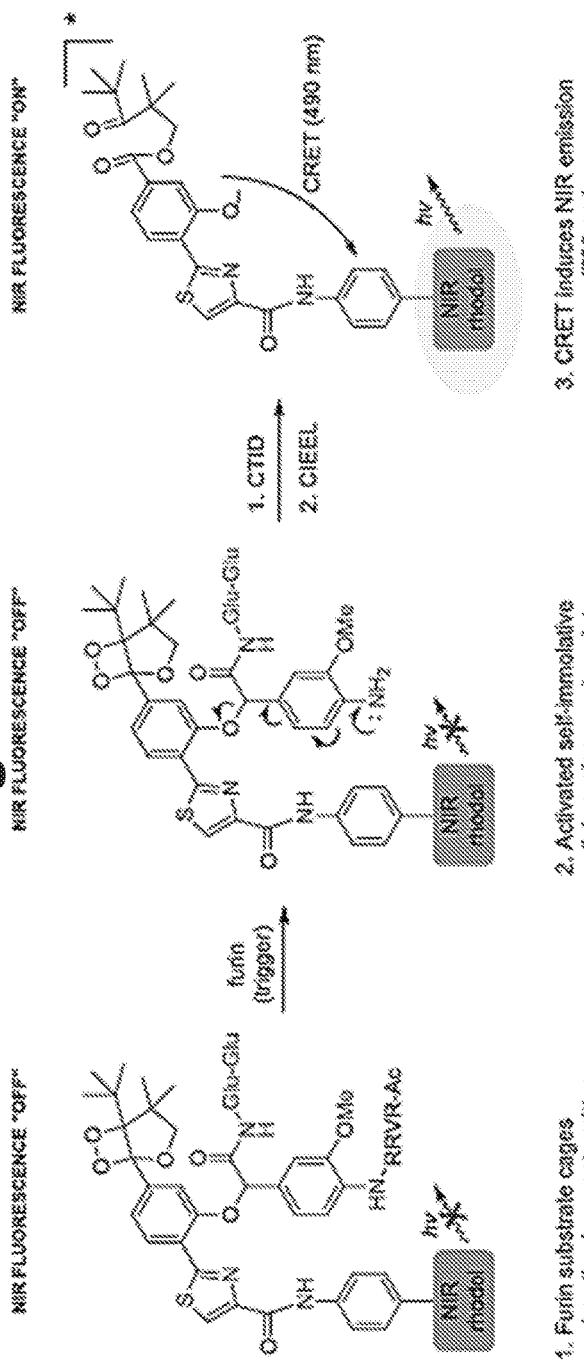
FIG. 12B illustrates the mechanism of NIR emission from a furin-activated NIR-emitting CRET probe incorporating an NIR rhodol of the disclosure.
Figure 14A:
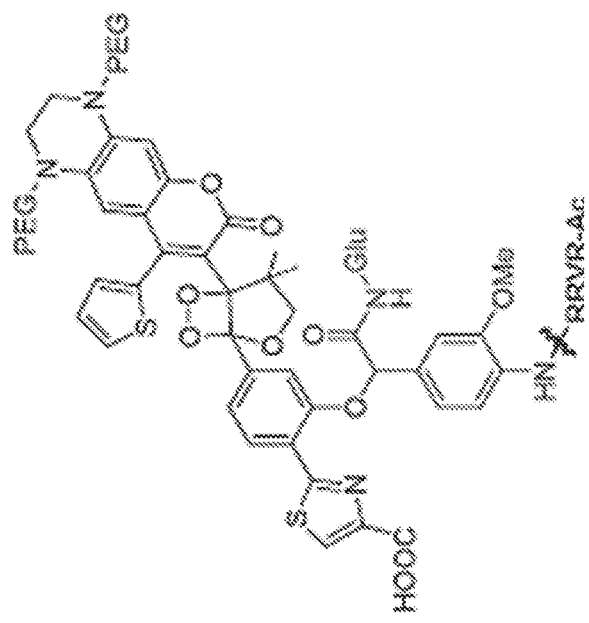
FIG. 14A illustrates an embodiment of a dual modal furin-activated NIR-emitting coumarin probe.
Figure 14B:
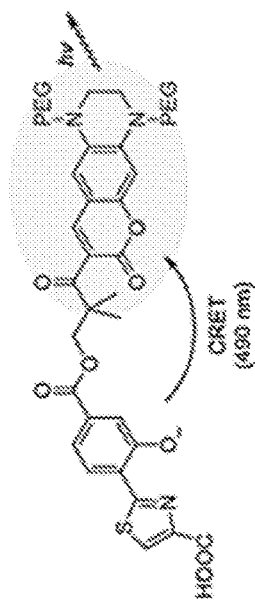
FIG. 14B illustrates the mechanism of NIR emission from a dual modal furin-activated NIR-emitting coumarin probe.
Figure 14B:
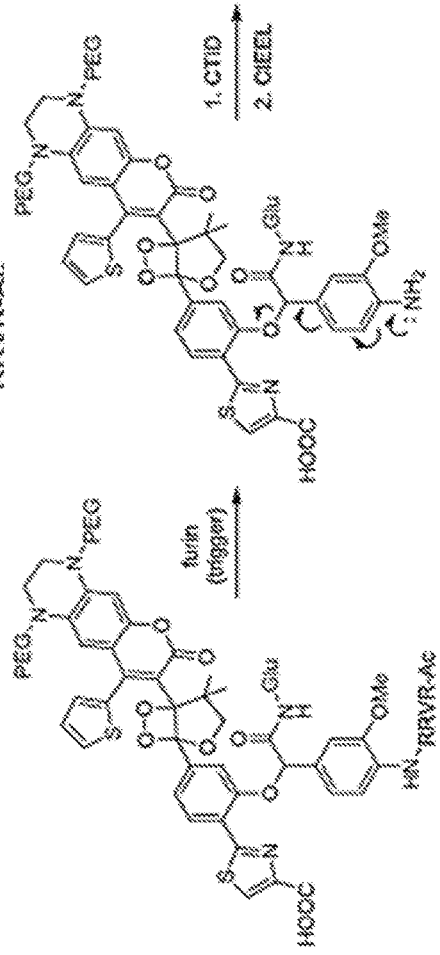
Figure 16:
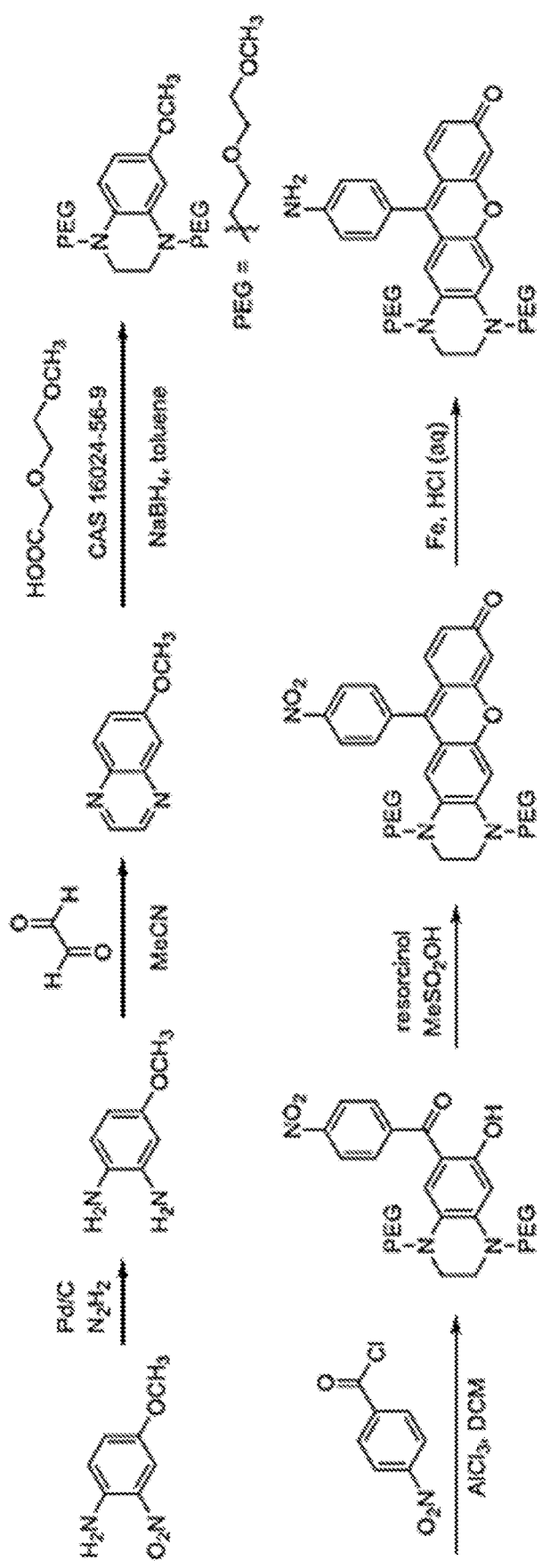
FIG. 16 illustrates the synthesis of a NIR-emitting rhodol.

Use as a Multimodal Probe (NIR Chemiluminescence, CRET, & PET):

Another example of multimodal use of the rhodol is in combination that allows both with CRET and PET imaging (FIG. 12B). This provides the low background as shown in FIG. 11B, but allows for PET imaging. In FIG. 12B, furin is an example of a representative enzyme that can activate the probe. Upon activation by cleavage of the probe by furin, the CL emitter transfers energy to the rhodol, which then emits at NIR wavelengths. Upon enzymatic cleavage, we envisage that the radiotracer component will be trapped in the Golgi, as per literature precedent.

Example 8

Figure 6:
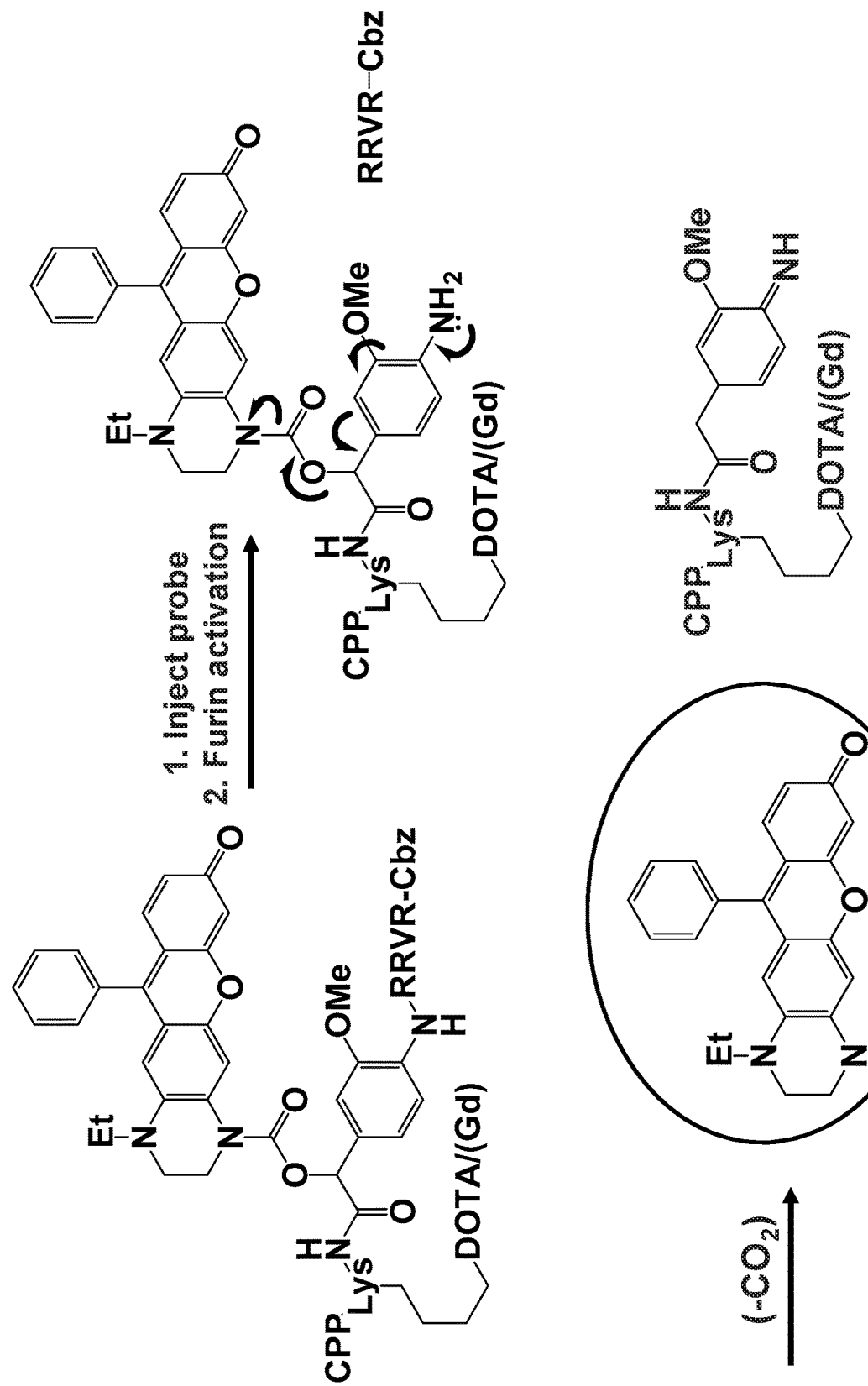
FIG. 6 illustrates an embodiment of a multimodal fluorescence/MR smart probe for furin activity. The probe consists of: a rhodol fluorophore, a self-immolative linker, an enzyme substrate, and an MRI contrast agent. The probe is first injected into the specimen. It will penetrate the blood-brain barrier (BBB) due to the cell penetrating peptide (CPP)/targeting ligand and enter the GBM cell to be cleaved by furin. Enzymatic cleavage activates the self-immolative linker which releases the fluorophore in its fluorescent form. RRVR=Arg-Arg-Val-Arg.

Use as a Multimodal Probe (NIR Fluorescence & MR):

The rhodol fluorophore can also be paired with MRI for bimodal imaging. In FIG. 6 is shown how the rhodol fluorophore could be incorporated into an MR probe.

Example 9

Figure 7:
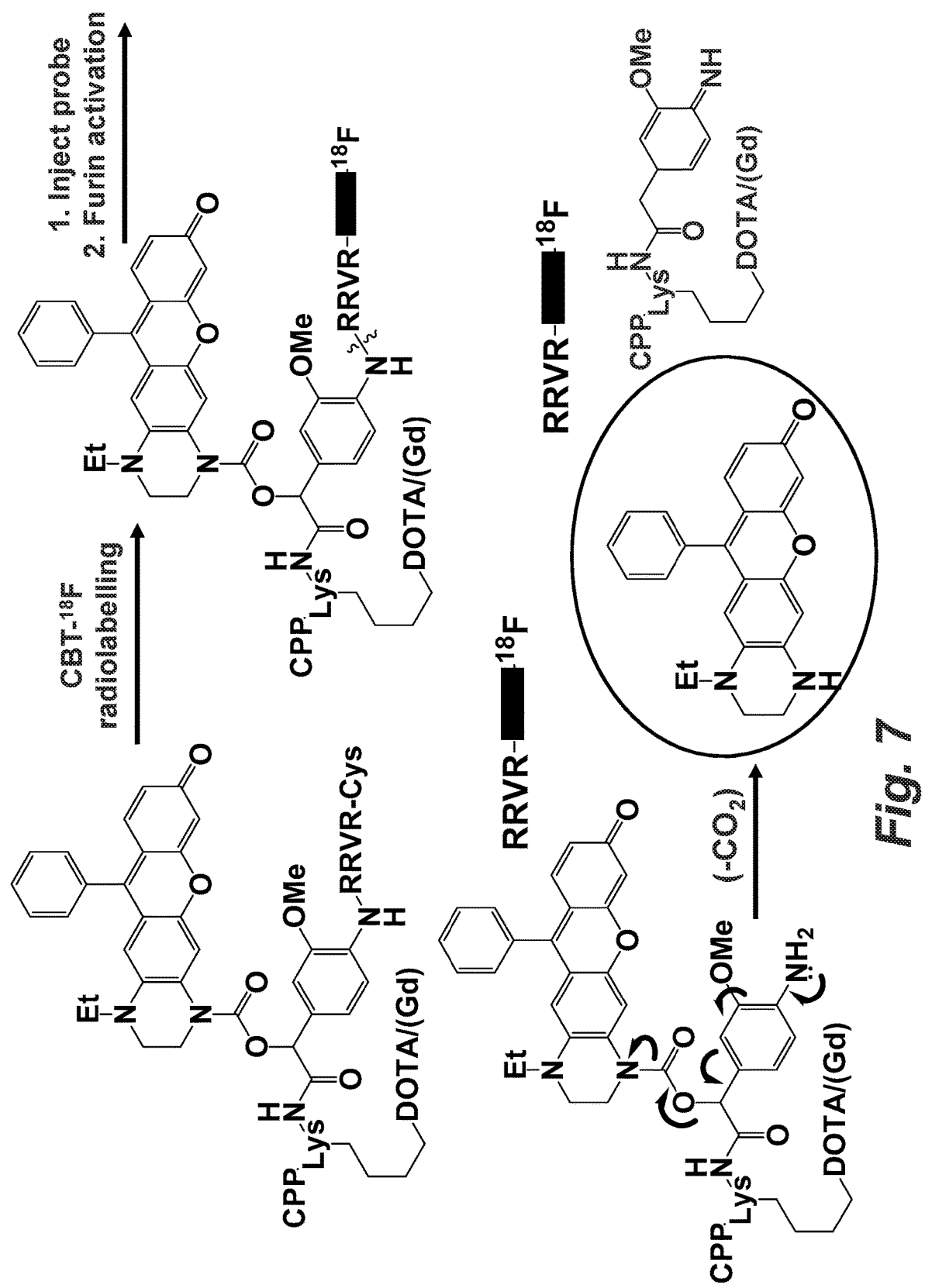
FIG. 7 illustrates an embodiment of a multimodal fluorescence/PET/MR smart probe for detecting furin activity. The probe consists of: a rhodol fluorophore, a self-immolative linker, an enzyme substrate, an MRI contrast agent, and a radioactive label. First, the non-fluorescent probe will be radiolabeled. Then, the probe will be injected into the specimen. It will penetrate the blood-brain barrier (BBB) due to the cell penetrating peptide (CPP)/targeting ligand and enter the GBM cell to be cleaved by furin. Enzymatic cleavage activates the self-immolative linker which releases the rhodol fluorophore in its fluorescent form. The cleaved radiolabel is positively charged (due to the arginines) and will stay trapped inside the cell causing accumulation and high contrast in the PET signal. RRVR=Arg-Arg-Val-Arg.

Use as a Multimodal Probe (NIR Fluorescence, PET, & MR):

The number of imaging modalities used depends on how much or what type of information the researcher is seeking. In FIG. 7 is shown a tri-modal enzyme-activatable molecular probe using fluorescence, PET, and MR.

Example 10

A major limitation to current chemiluminescent and bioluminescent probes is the emission of light with extremely short lifetimes and short wavelengths (i.e., less than 650 nm), that prohibits the use of the probes for high-throughput analyses and deep tissue imaging. Embodiments are provided of a multi-modal probe, advantageous for the detection of an enzyme such as, but not limited to, furin that combines near-infrared (NIR) chemiluminescent emission (i.e., greater than 650 nm) with positron emission tomography (PET) can provide high contrast imaging of upregulated enzymatic activity. Accordingly, the disclosure describes multi-modal imaging probes that use enzyme-triggered activation of chemiluminescent 1,2-dioxetanes for generating the emission of NIR light, and ii) accumulation of a radiolabel ($^{18}$F) for the purpose of imaging furin activity in glioblastoma.

Figure 8:
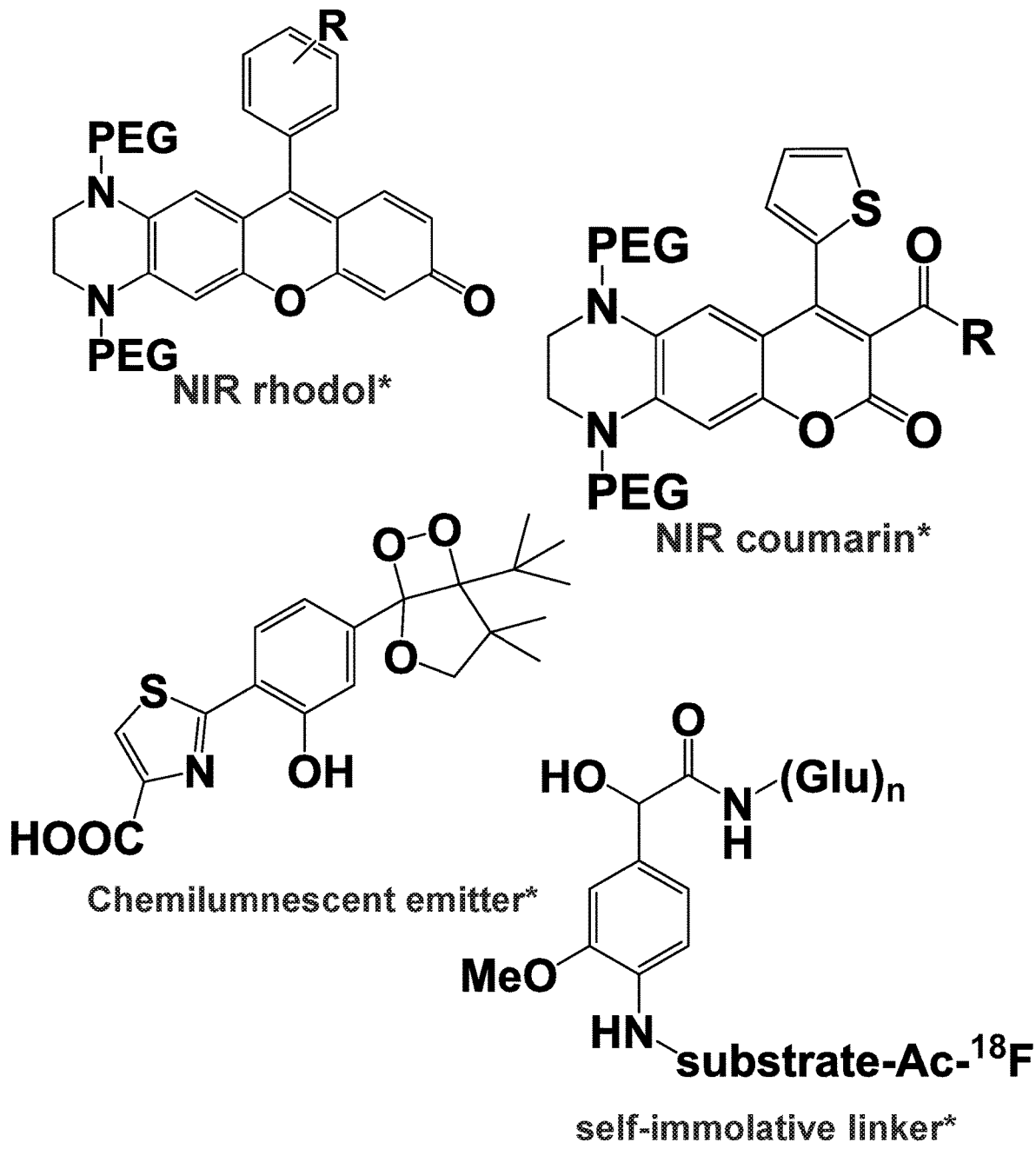
FIG. 8 illustrates molecular structures of modular components for probes according to the disclosure.
Figure 17:
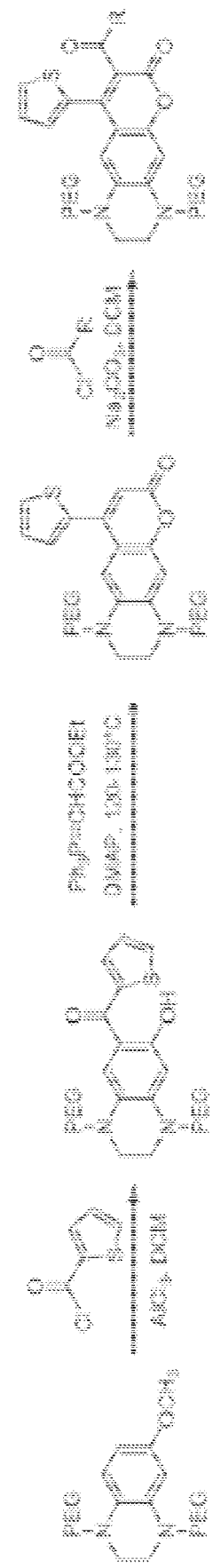
FIG. 17 illustrates the synthesis of a NIR-emitting coumarin.
Figure 18:
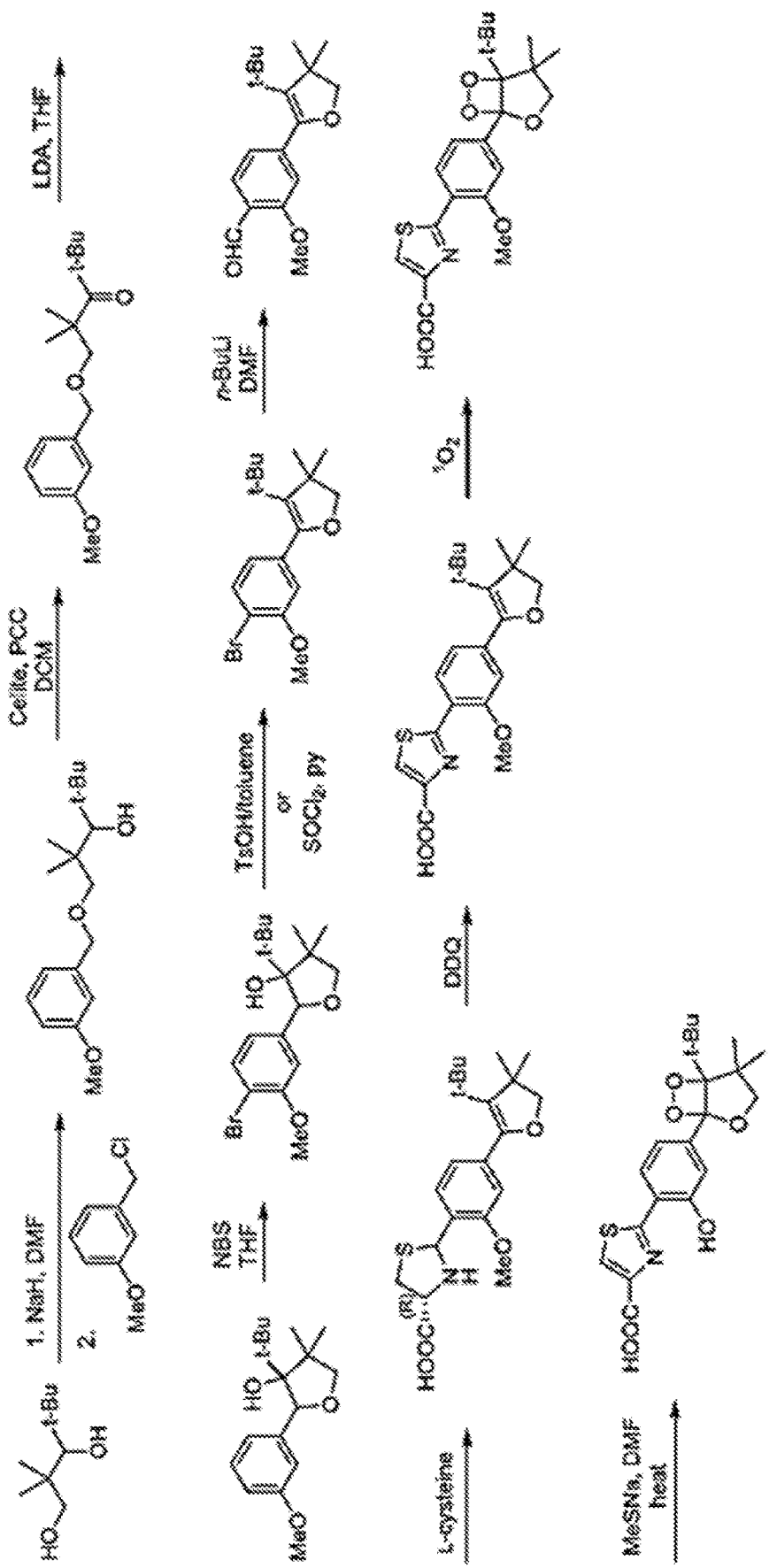
FIG. 18 illustrates the synthesis of a chemiluminescent emitter not integrated with a fluorophore of the disclosure.
Figure 19:
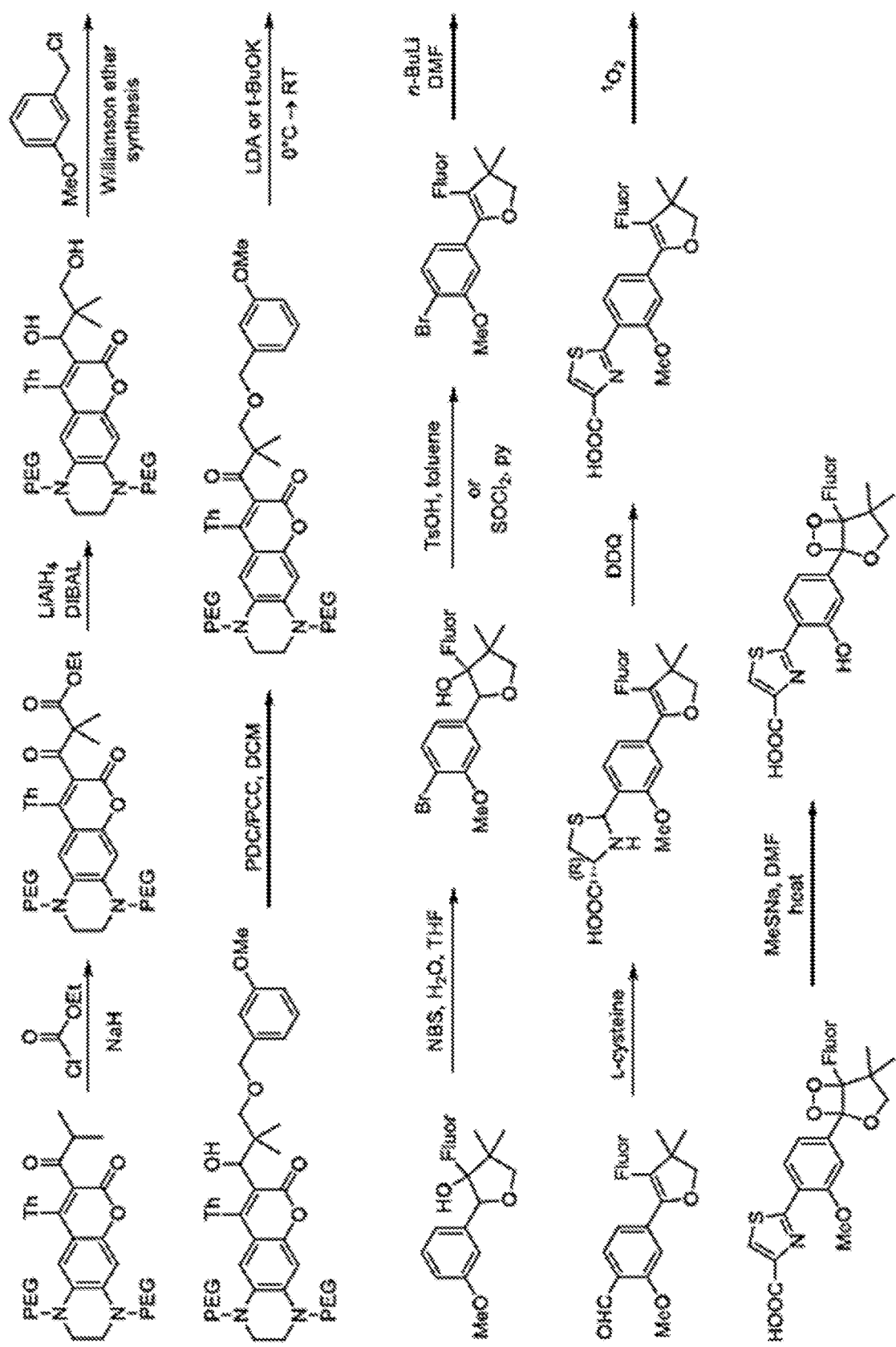
FIG. 19 illustrates the synthesis of a chemiluminescent emitter integrated with a fluorophore of the disclosure.
Figure 20:
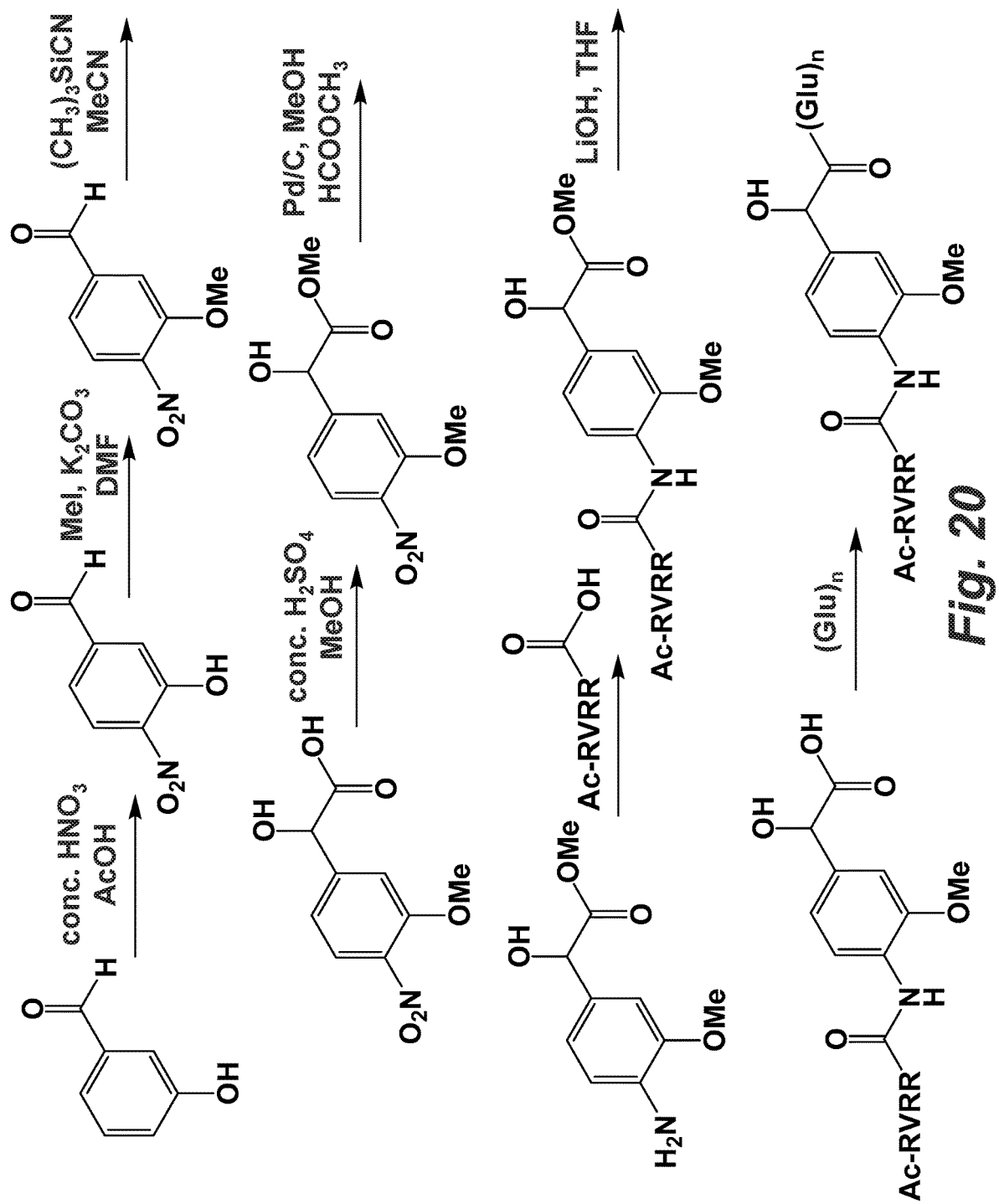
FIG. 20 illustrates the synthesis of a self-immolative linker.

FIG. 8 illustrates examples of the molecular moieties that may be combined and conjugated to form a probe probes. Synthesis of a coumarin suitable for incorporating into the probes of the disclosure is shown schematically in FIG. 17

The multimodal imaging probes consist of a maximum of three molecular components: either a NIR-emitting rhodol or coumarin fluorophore with a 200 nm Stokes shift, a chemiluminescent emitter, and a self-immolative linker with a cleavable $^{18}$F peptide substrate (FIG. 8). The synthesis for the probes is modular and allows for convenient attachment of different fluorophores or enzymatic peptide substrates. As a result, the system can be tailored to image specific enzymatic activity by a mere modification of the substrate that appends to the self-immolative linker. For example, the enzyme-cleavable peptide may be any peptide known in the art that is specifically recognized by a peptidase that will cleave a bond between the probe and the self-immolative linker to release the peptide therefrom.

We claim:

1. A multimodality probe, wherein said probe is formula A, B, C, or D, wherein said formulae are:

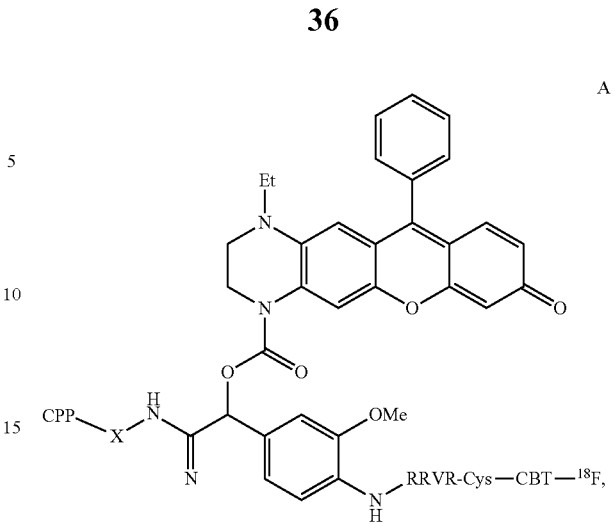

wherein X is cysteic acid,

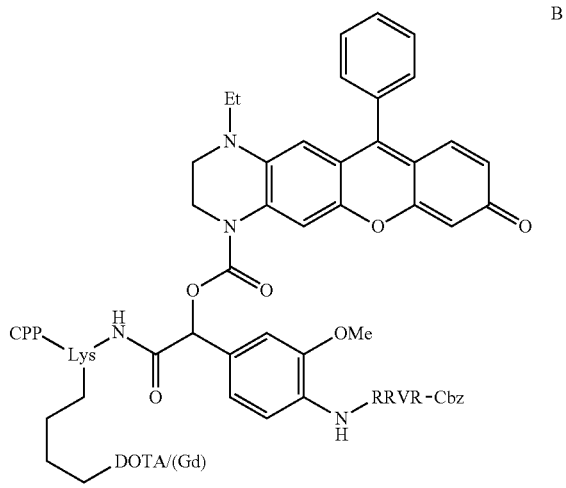

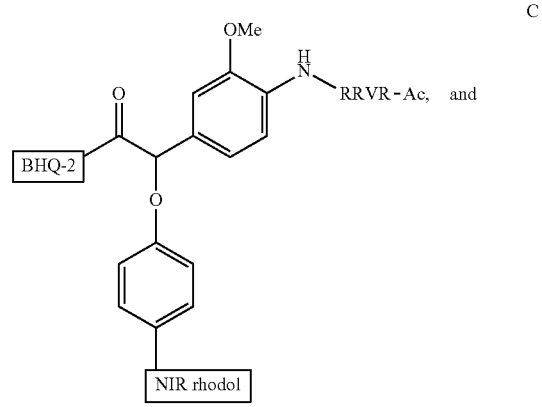

-continued
D
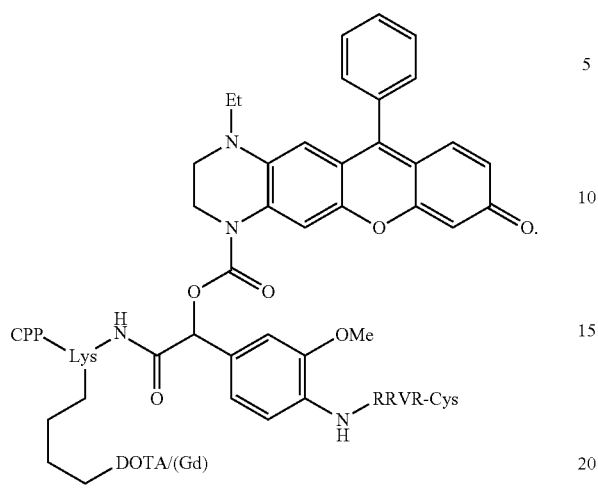
* * * * *